US010213226B2

United States Patent
Vreeman

(10) Patent No.: US 10,213,226 B2
(45) Date of Patent: *Feb. 26, 2019

(54) TISSUE-REMOVING CATHETER INCLUDING URGING MECHANISM

(71) Applicant: Covidien LP, Mansfield, MA (US)

(72) Inventor: Daniel J. Vreeman, Otsego, MN (US)

(73) Assignee: Covidien LP, Alpine, MA (US)

( * ) Notice: Subject to any disclaimer, the term of this patent is extended or adjusted under 35 U.S.C. 154(b) by 13 days.

This patent is subject to a terminal disclaimer.

(21) Appl. No.: 15/348,724

(22) Filed: Nov. 10, 2016

(65) Prior Publication Data

US 2017/0056046 A1  Mar. 2, 2017

Related U.S. Application Data

(63) Continuation of application No. 14/101,994, filed on Dec. 10, 2013, now Pat. No. 9,532,797.

(Continued)

(51) Int. Cl.
*A61B 17/22* (2006.01)
*A61B 17/3207* (2006.01)
(Continued)

(52) U.S. Cl.
CPC .... *A61B 17/3207* (2013.01); *A61B 17/00234* (2013.01); *A61B 17/320783* (2013.01);
(Continued)

(58) Field of Classification Search
CPC .......... A61B 17/32002; A61B 17/3207; A61B 17/320758; A61B 17/320783;
(Continued)

(56) References Cited

U.S. PATENT DOCUMENTS 4,290,427 A 9/1981 Chin
4,631,052 A 12/1986 Kensey
(Continued)

FOREIGN PATENT DOCUMENTS

WO 2010045226 A2 4/2010
WO 2012003430 A2 1/2012

OTHER PUBLICATIONS

International Search Report for related Application No. PCT/US2013/073507, Dated Apr. 6, 2014, 5 pages, Rijswijk, The Netherlands.
(Continued)

*Primary Examiner* — Melanie R Tyson
(74) *Attorney, Agent, or Firm* — Stinson Leonard Street LLP

(57) ABSTRACT

A tissue-removing catheter includes an elongate catheter body. The catheter body has a jogged portion that applies an urge force against a body lumen wall and urges a portion of the catheter body toward a portion of the body lumen wall. A tissue-removing element removes tissue from the body lumen during the cutting operation. The tissue-removing element is located generally adjacent the portion of the catheter body that is urged toward the body lumen wall by the jogged portion. An urging mechanism selectively applies a compressive load to the catheter body to adjust the bending stiffness of the jogged portion and the urge force applied by the jogged portion.

19 Claims, 27 Drawing Sheets

Related U.S. Application Data

(60) Provisional application No. 61/736,185, filed on Dec. 12, 2012.

(51) Int. Cl.
*A61B 17/00* (2006.01)
*A61D 1/02* (2006.01)

(52) U.S. Cl.
CPC .............. *A61B 2017/003* (2013.01); *A61B 2017/00292* (2013.01); *A61B 2017/320741* (2013.01); *A61B 2017/320791* (2013.01)

(58) Field of Classification Search
CPC ....... A61B 2017/320741; A61B 2017/320791; A61B 2017/32003
USPC .................... 606/159, 167, 170, 171, 180
See application file for complete search history.

(56) References Cited

U.S. PATENT DOCUMENTS

| | | |
|---|---|---|
| 4,765,332 A | 8/1988 | Fischell et al. |
| 4,790,813 A | 12/1988 | Kensey |
| 4,926,858 A | 5/1990 | Gifford, III et al. |
| 4,950,277 A | 8/1990 | Farr |
| 5,026,383 A | 6/1991 | Nobles |
| 5,085,662 A | 2/1992 | Willard |
| 5,100,424 A | 3/1992 | Jang et al. |
| 5,123,904 A | 6/1992 | Shimomura et al. |
| 5,176,693 A | 1/1993 | Pannek, Jr. |
| 5,192,291 A | 3/1993 | Pannek, Jr. |
| 5,226,909 A | 7/1993 | Evans et al. |
| 5,242,460 A | 9/1993 | Klein et al. |
| 5,350,390 A | 9/1994 | Sher |
| 5,507,760 A | 4/1996 | Wynne et al. |
| 5,507,795 A | 4/1996 | Chiang et al. |
| 5,556,408 A | 9/1996 | Farhat |
| 5,569,277 A | 10/1996 | Evans et al. |
| 5,601,580 A | 2/1997 | Goldberg et al. |
| 5,620,456 A | 4/1997 | Sauer et al. |
| 5,776,156 A | 7/1998 | Shikhman |
| 5,857,982 A | 1/1999 | Milliman et al. |
| 6,053,923 A | 4/2000 | Veca et al. |
| 6,068,603 A | 5/2000 | Suziki |
| 6,110,127 A | 8/2000 | Suziki |
| 6,428,539 B1 | 8/2002 | Baxter et al. |
| 6,503,263 B2 | 1/2003 | Adams |
| RE38,018 E | 3/2003 | Anctil et al. |
| 6,579,298 B1 | 6/2003 | Bruneau et al. |
| RE38,335 E | 11/2003 | Aust et al. |
| 7,329,267 B2 | 2/2008 | Weber |
| 7,344,546 B2 | 3/2008 | Wulfman et al. |
| 7,485,125 B2 | 2/2009 | Sjostrom |
| 7,520,886 B2 | 4/2009 | Surti |
| 7,635,340 B2 | 12/2009 | Vetter et al. |
| 7,699,790 B2 | 4/2010 | Simpson |
| 7,862,518 B2 | 1/2011 | Parihar |
| 7,918,803 B2 | 4/2011 | Ritchart et al. |
| 7,927,784 B2 | 4/2011 | Simpson |
| 7,951,161 B2 | 5/2011 | Bonnette et al. |
| 7,981,128 B2 | 7/2011 | To et al. |
| 8,012,164 B1 | 9/2011 | Donohoe et al. |
| 8,052,704 B2 | 11/2011 | Olson |
| 8,062,316 B2 | 11/2011 | Patel et al. |
| 8,070,762 B2 | 12/2011 | Escudero et al. |
| 9,532,797 B2 * | 1/2017 | Vreeman ............ A61B 17/3207 |
| 2004/0006358 A1 | 1/2004 | Wulfman et al. |
| 2004/0167553 A1* | 8/2004 | Simpson ........ A61B 17/320758 606/159 |
| 2006/0235366 A1 | 10/2006 | Simpson |
| 2007/0055259 A1 | 3/2007 | Norton et al. |
| 2007/0276419 A1 | 11/2007 | Rosenthal |
| 2007/0282358 A1 | 12/2007 | Remiszewski et al. |
| 2008/0045986 A1 | 2/2008 | To et al. |
| 2008/0065124 A1 | 3/2008 | Olson |
| 2008/0140104 A1 | 6/2008 | Bender et al. |
| 2009/0234378 A1* | 9/2009 | Escudero ....... A61B 17/320758 606/180 |
| 2010/0198240 A1 | 8/2010 | Simpson et al. |
| 2011/0004107 A1 | 1/2011 | Rosenthal et al. |
| 2011/0087258 A1 | 4/2011 | Sluss |
| 2011/0130777 A1 | 6/2011 | Zhang et al. |
| 2011/0144673 A1 | 6/2011 | Zhang et al. |
| 2011/0152906 A1 | 6/2011 | Escudero et al. |
| 2011/0190801 A1 | 8/2011 | Mark et al. |
| 2011/0301626 A1 | 12/2011 | To et al. |
| 2011/0306995 A1 | 12/2011 | Moberg |

OTHER PUBLICATIONS

Non-Final Office action for U.S. Appl. No. 14/101,994, dated Dec. 23, 2015, 8 pages.
Non-Final Office action for U.S. Appl. No. 14/101,994, dated Apr. 18, 2016, 6 pages.
Japanese Notice of Reasons for Rejection for Application No. 2015-547433, dated Jun. 1, 2016, 7 pages, with English translation.
Japanese Notice of Notice of Final Rejection for Application No. 2015-547433, dated Jun. 1, 2016, 7 pages, with English translation.

* cited by examiner

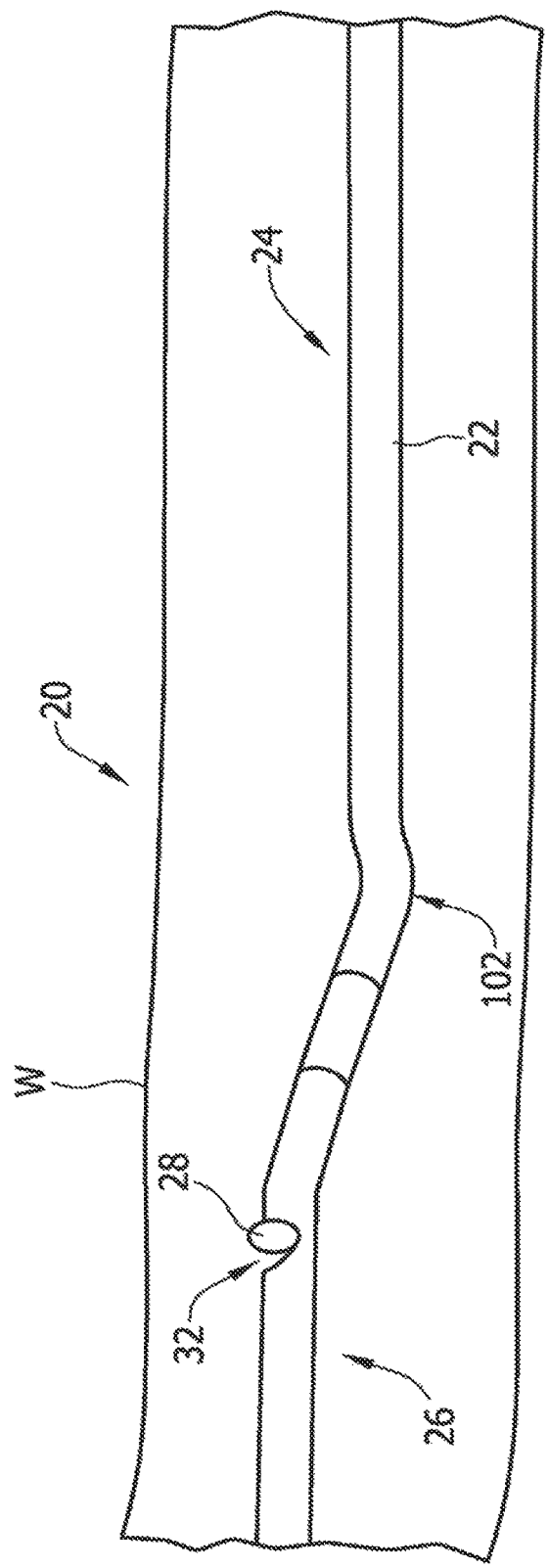

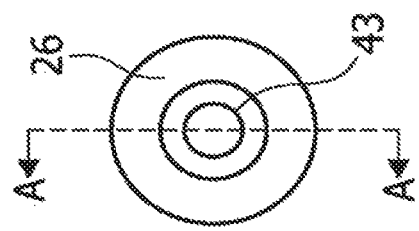
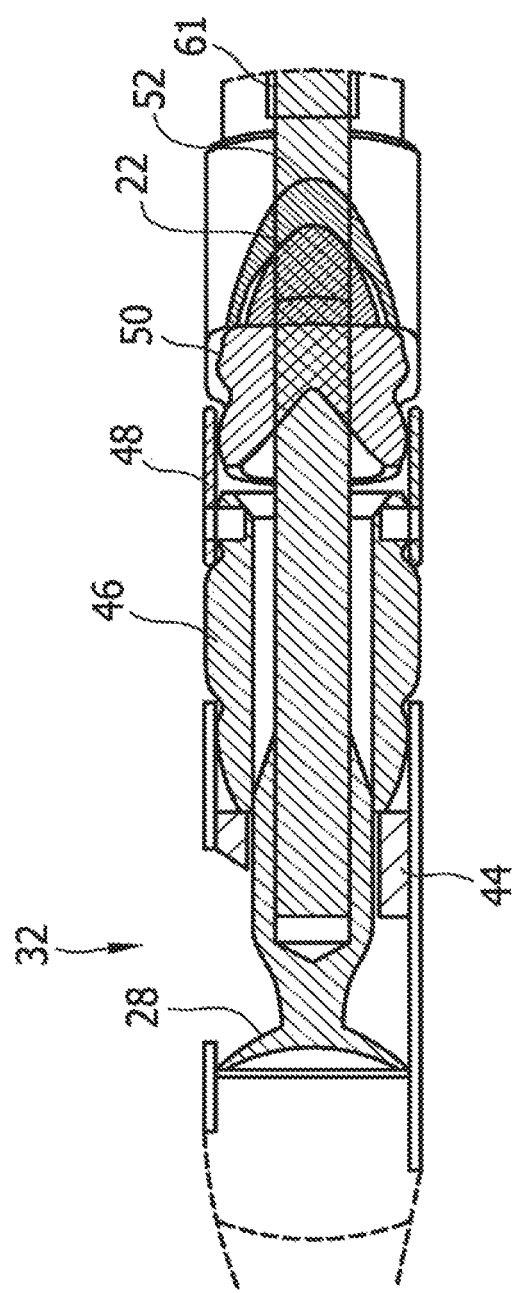
FIG. 3A
FIG. 3B

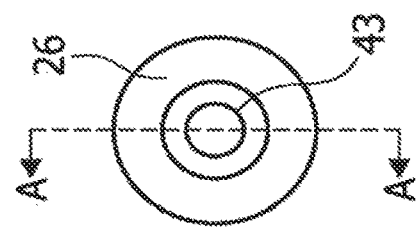
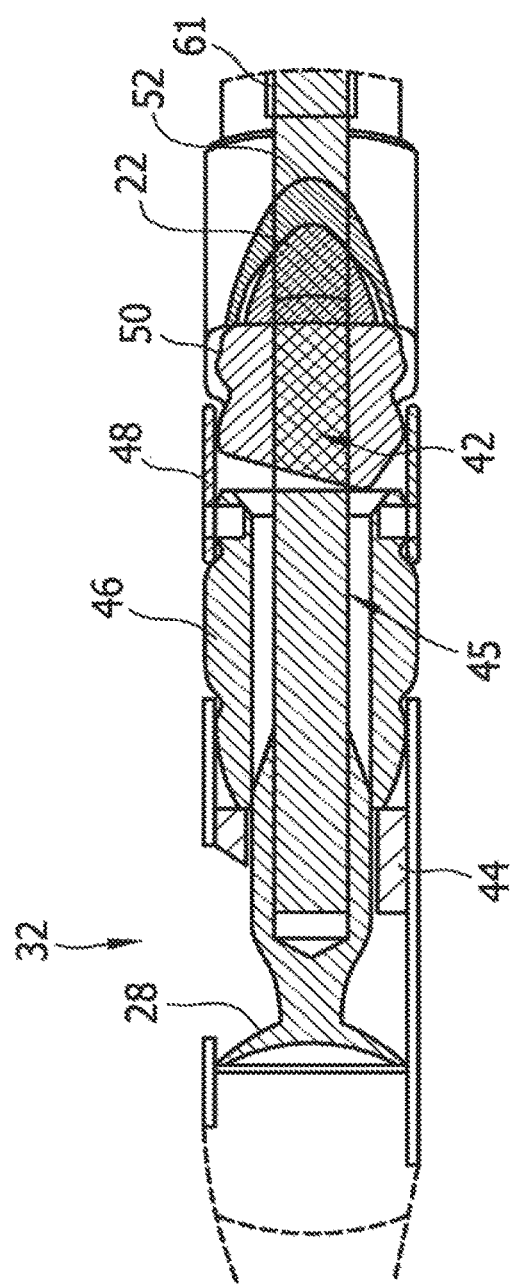
FIG. 3C
FIG. 3D

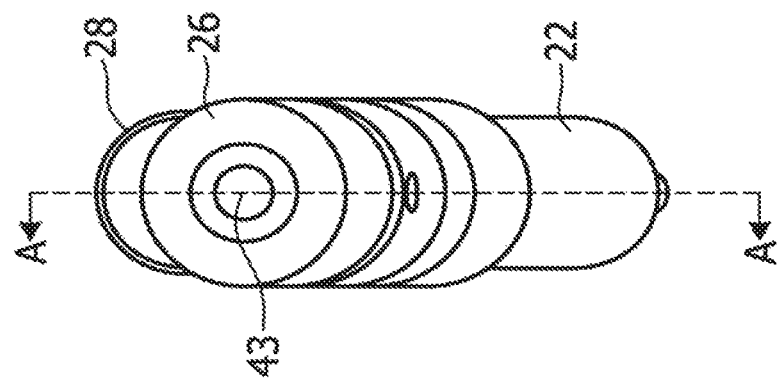
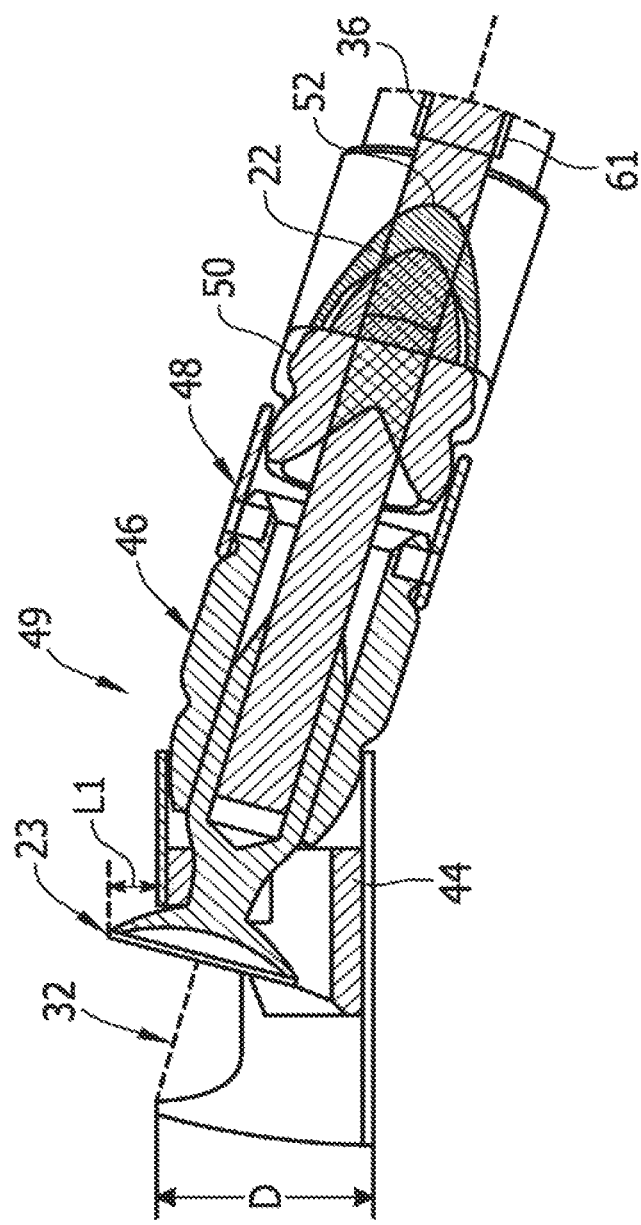

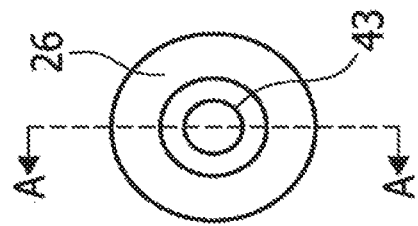
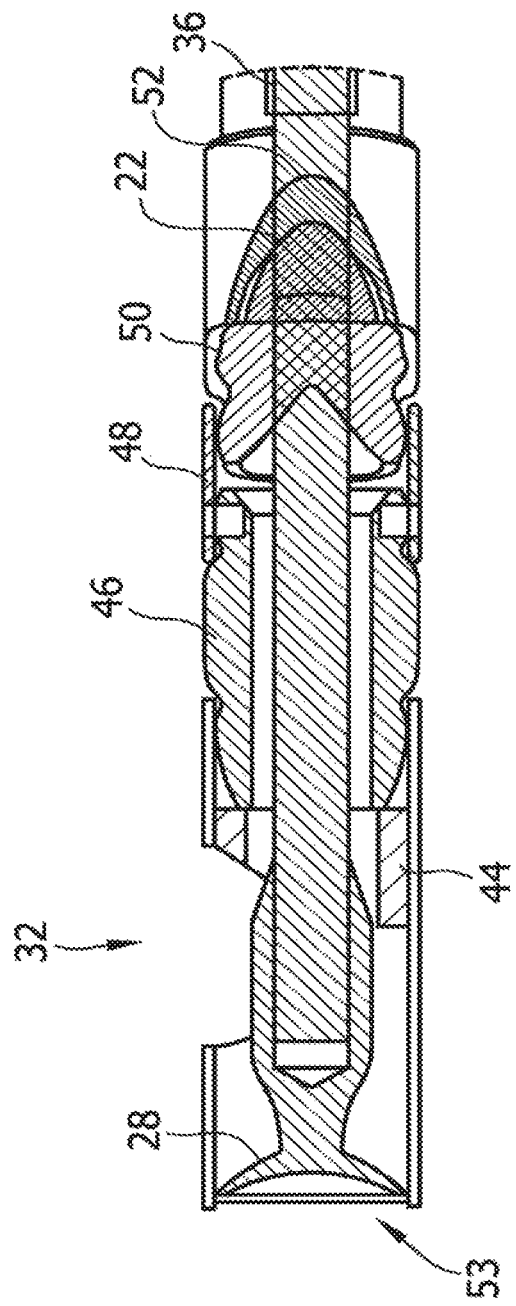
FIG. 5A
FIG. 5B

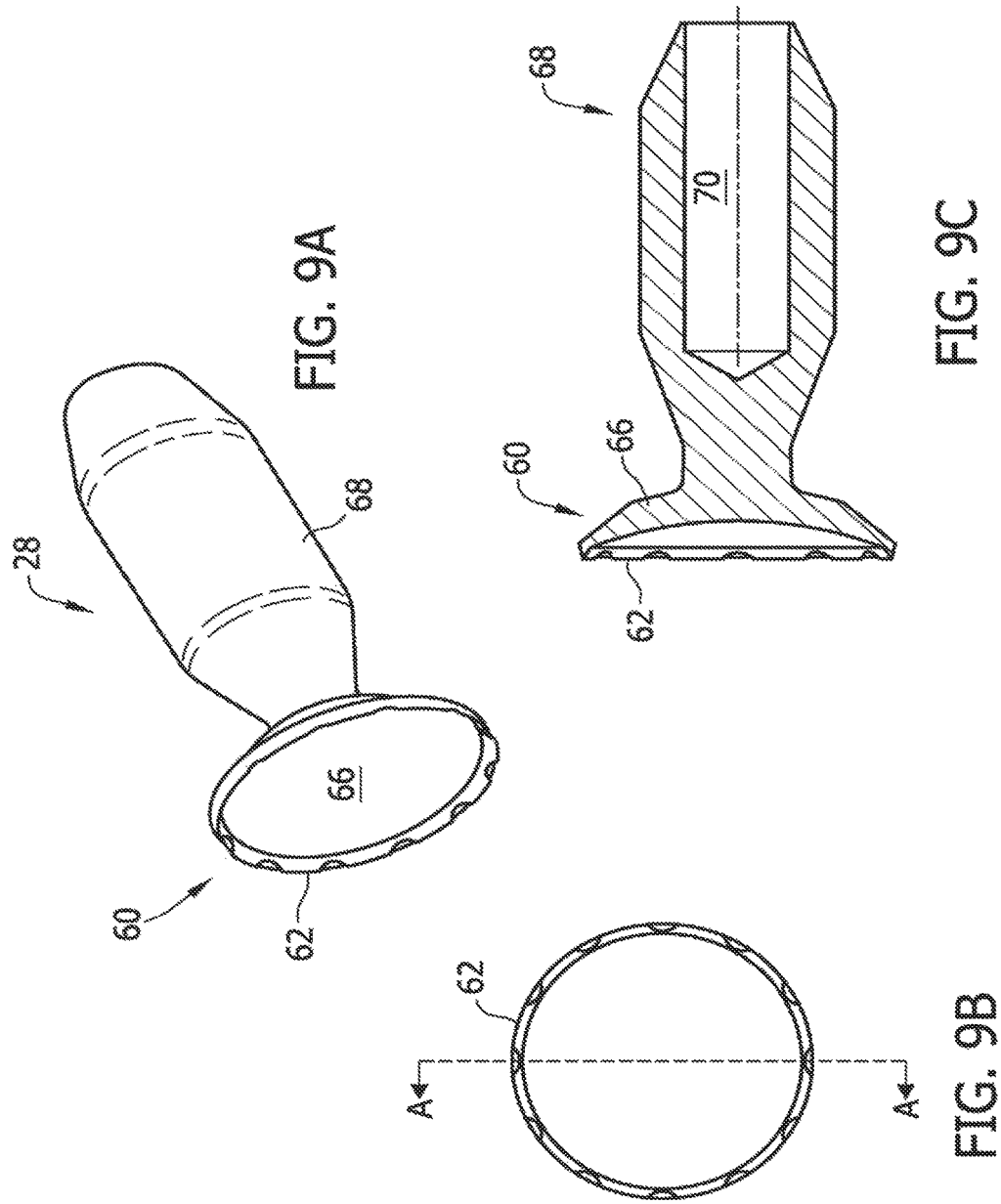

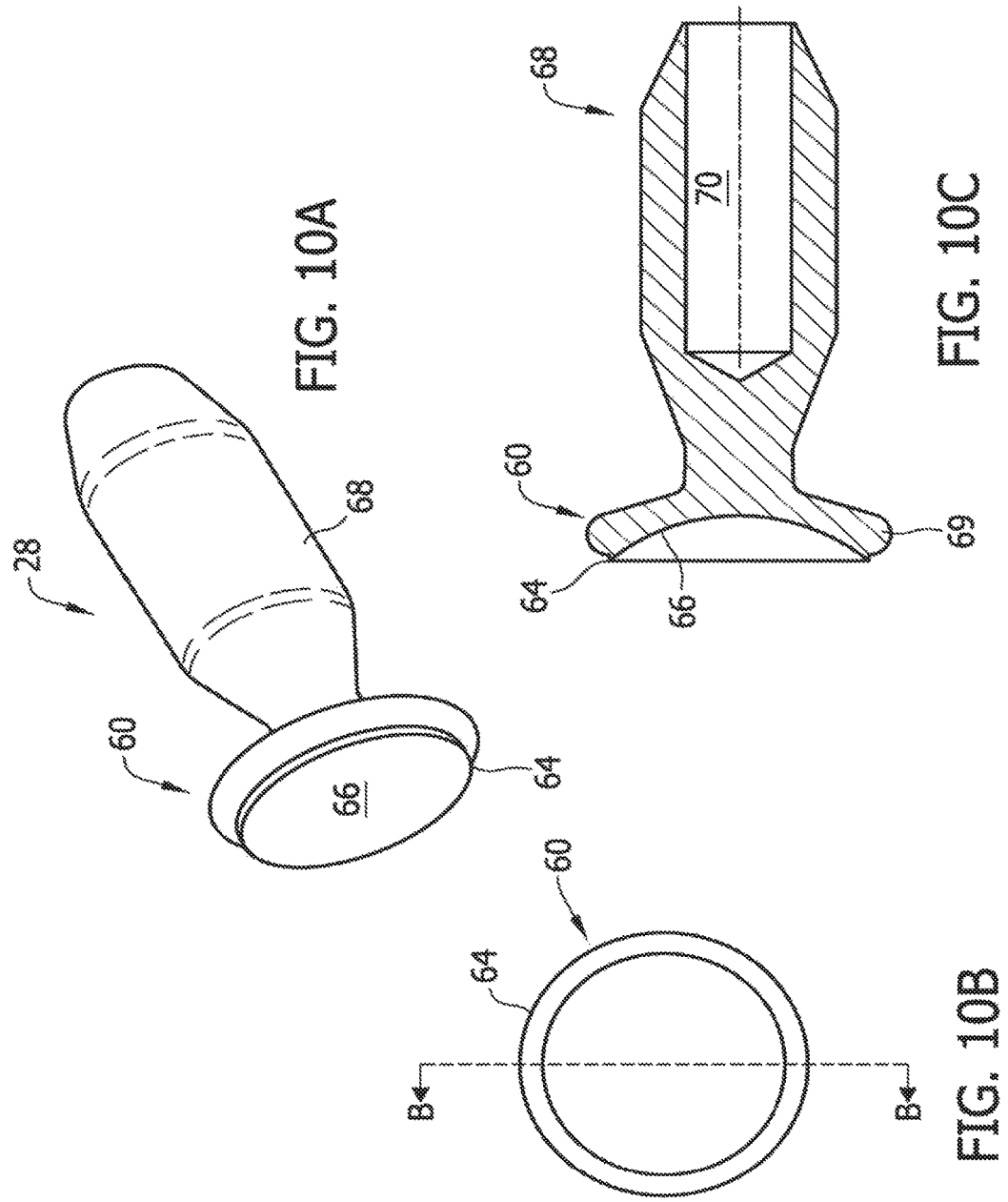

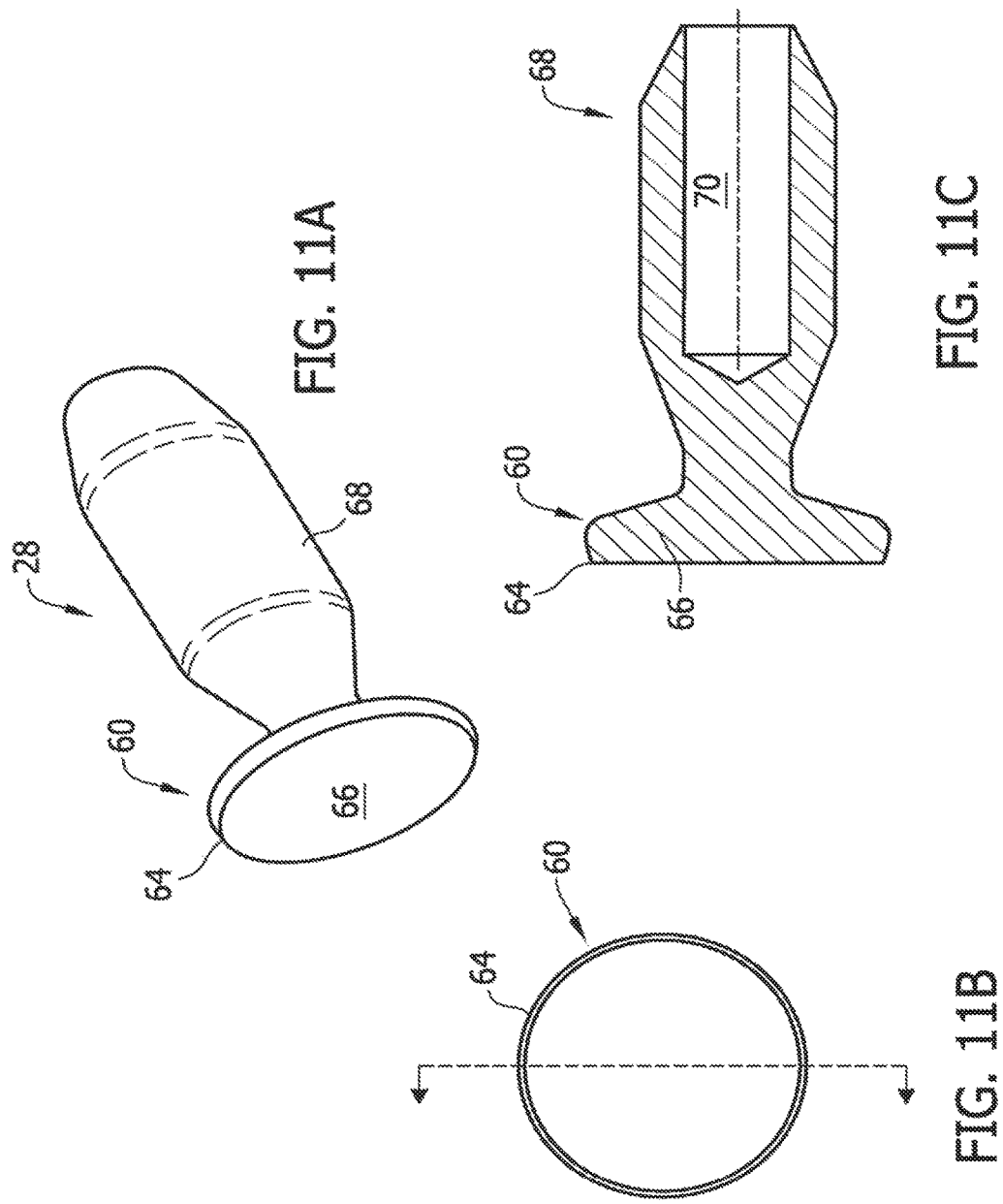

TISSUE-REMOVING CATHETER INCLUDING URGING MECHANISM

CROSS-REFERENCE TO RELATED APPLICATIONS

The present application is a continuation of U.S. application Ser. No. 14/101,994, filed Dec. 10, 2003, issued as U.S. Pat. No. 9,532,797, which claims priority to U.S. Provisional Application Ser. No. 61/736,185, filed Dec. 12, 2012, the entirety of each of which is hereby incorporated by reference.

FIELD OF THE DISCLOSURE

The present invention generally relates to a tissue-removing catheter for removing tissue from a body lumen including an operational control mechanism.

BACKGROUND

Vascular disease frequently arises from the accumulation of atheromatous material on the inner walls of vascular lumens, particularly arterial lumens of the peripheral and other vasculature, especially peripheral arteries, resulting in a condition known as atherosclerosis. Atherosclerosis occurs naturally as a result of aging, but may also be aggravated by factors such as diet, hypertension, heredity, vascular injury, and the like. Atheromatous deposits can have widely varying properties, with some deposits being relatively soft and others being fibrous and/or calcified. In the latter case, the deposits are frequently referred to as plaque.

Vascular disease can be treated in a variety of ways, including drugs, bypass surgery, and a variety of catheter-based approaches, including those which rely on intravascular tissue-removing or removal of the atheromatous or other material occluding a blood vessel. A variety of methods for cutting or dislodging material and removing such material from the blood vessel have been proposed, generally being referred to as atherectomy procedures. Atherectomy catheters intended to cut or excise material from the blood vessel lumen may employ a rotatable cutting blade (or other tissue-removing element) which can be advanced into or past the occlusive material in order to cut and separate such material from the blood vessel lumen.

It is desirous to provide catheters which can access small, tortuous regions of body lumens and which can remove tissue and/or other occluding materials from within body lumens in a controlled fashion. In one instance, it may be desired to provide atherectomy catheters which can facilitate capturing atheromatous materials. The catheters and methods for use in a variety of body lumens, including but not limited to coronary, peripheral, and other arteries, and other body lumens.

SUMMARY

In one aspect, a tissue-removing catheter includes an elongate catheter body. The catheter body has a jogged portion that applies an urge force against a body lumen wall and urges a portion of the catheter body toward a portion of the body lumen wall. A tissue-removing element removes tissue from the body lumen during the cutting operation. The tissue-removing element is located generally adjacent the portion of the catheter body that is urged toward the body lumen wall by the jogged portion. An urging mechanism selectively applies a compressive load to the catheter body to adjust the bending stiffness of the jogged portion and the urge force applied by the jogged portion.

Other features will be in part apparent and in part pointed out hereinafter.

BRIEF DESCRIPTION OF THE DRAWINGS

FIG. 1A is a side view of a portion of a tissue-removing catheter as in FIG. 1, shown in a body lumen, where the body has a rigid distal portion with a bend, according to one embodiment of the present invention;

FIG. 3A is an end view of the distal portion of the tissue-removing catheter of FIG. 1 in which the tissue-removing element is in a closed position in the catheter body;

FIG. 3B is a sectional view along line A-A of FIG. 3A;

FIGS. 3C and 3D are views of the distal portion of a tissue-removing catheter similar to FIGS. 3A and 3B, where the distal portion has a locking shuttle mechanism;

FIG. 4A is an end view of the distal portion of the tissue-removing catheter of FIG. 1 in which the tissue-removing element is in an open position outside of the cutting window;

FIG. 4B is a sectional view along Line A-A of FIG. 4A;

FIG. 5A is an end view of the distal portion of the tissue-removing catheter of FIG. 1 in which the tissue-removing element is in a packing position within a tip of the catheter;

FIG. 5B is a sectional view along line A-A of FIG. 5A;

FIG. 9A is a perspective view of a tissue-removing element of the present invention;

FIG. 9B is an end view of the tissue-removing element of FIG. 9A;

FIG. 9C is a sectional view of the tissue-removing element along line A-A of the tissue-removing element of FIG. 9B;

FIG. 10A is a perspective view of a tissue-removing element;

FIG. 10B is an end view of the tissue-removing element of FIG. 10A;

FIG. 10C is a sectional view of the tissue-removing element along line B-B of the tissue-removing element of FIG. 10B;

FIG. 11A is a perspective view of another tissue-removing element;

FIG. 11B is an end view of the tissue-removing element of FIG. 11A;

FIG. 11C is a sectional view of the tissue-removing element along line C-C of the tissue-removing element of FIG. 11B;

Corresponding reference characters indicate corresponding parts throughout the drawings.

DETAILED DESCRIPTION OF THE DRAWINGS

Figure 1:
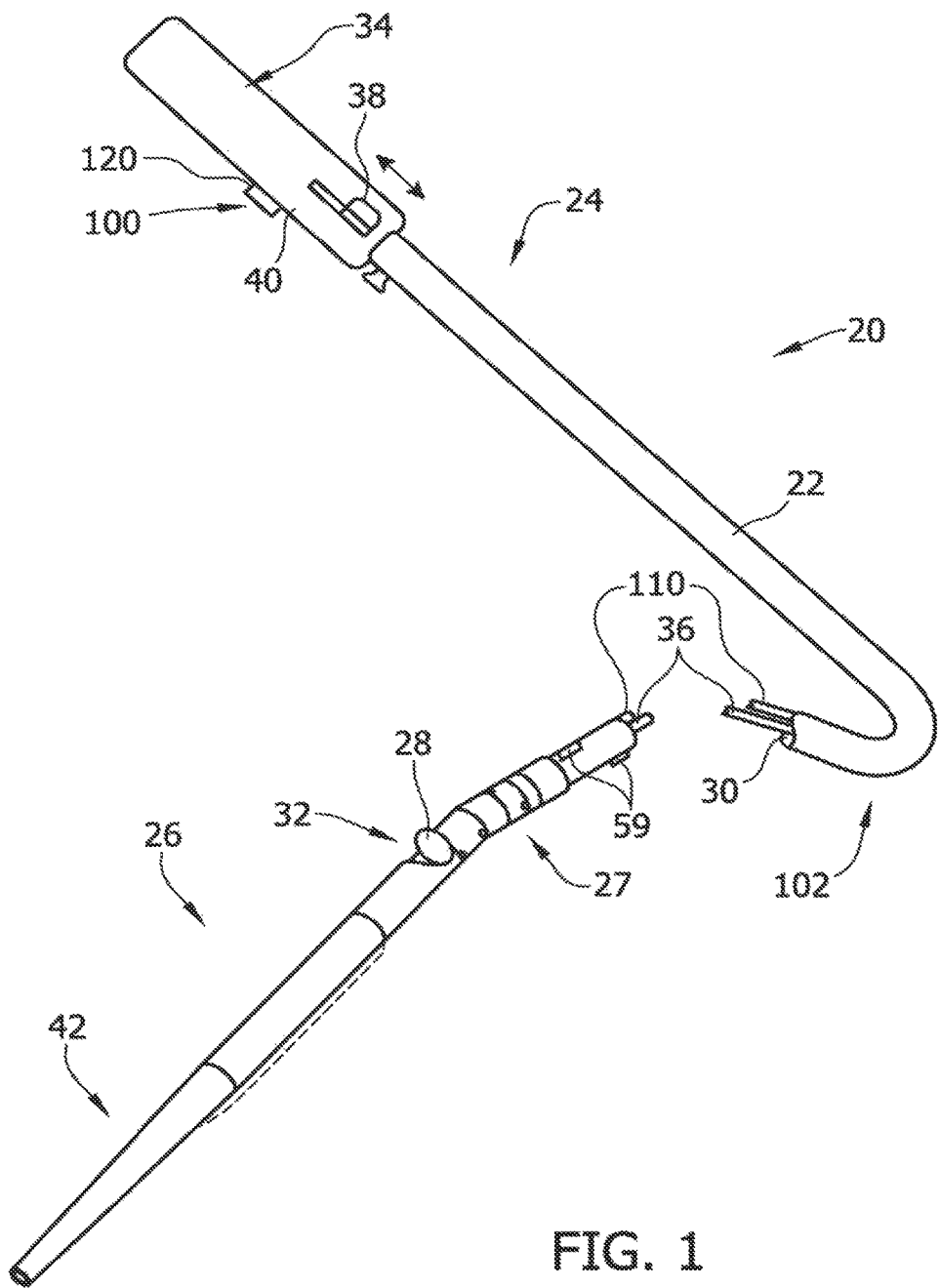
FIG. 1 is a perspective view of one embodiment of a tissue-removing catheter.

Referring now to the drawings, several embodiments of a tissue-removing catheter that removes tissue from a body lumen wall are disclosed. The illustrated catheter are particularly suited for removing (i.e., excising) an atheroma (i.e., plaque) from an arterial wall, such as a peripheral artery (e.g., a leg artery). The disclosed catheters, however, may also be suitable for treating stenoses of other body lumens and other hyperplastic and neoplastic conditions in other body lumens, such as the ureter, the biliary duct, respiratory passages, the pancreatic duct, the lymphatic duct, and the like. Neoplastic cell growth will often occur as a result of a tumor surrounding and intruding into a body lumen. Removal of such material can thus be beneficial to maintain patency of the body lumen. While the remaining discussion is directed toward atherectomy catheters for removing tissue and passing through atheromatous or thrombotic occlusive material in an artery, it will be appreciated that the catheters may be suitable for removing and/or passing through a variety of occlusive, stenotic, or hyperplastic material in a variety of body lumens.

Referring now to FIGS. 1-16, one non-limiting example of a suitable atherectomy catheter is generally indicated at 20. The illustrated catheter 20 comprises a catheter body 22 having a proximal portion 24 and a distal portion 26. Proximal portion 24 can be coupled to distal portion 26 with a connection assembly 27 to allow pivoting or deflection of distal portion 26 relative to proximal portion 24. A tissue-removing element 28, such as a cutter, as illustrated, is disposed within a lumen 30 of the catheter body 22. The tissue-removing element 28 removes tissue from the lesion or obstruction. It is understood that the tissue-removing element 28 may be another type of element for removing tissue, other than the illustrated cutter, including for example, an abrasive element (e.g., a burr). The cutter 28 is typically rotatable within the distal portion 26 about an axis that is generally parallel to the longitudinal axis of the distal portion 26 of catheter 20 and axially movable along the longitudinal axis. The cutter 28 can access target tissue through a side opening window 32 in the distal portion 26, which is typically large enough to allow the cutter 28 to protrude through and move out of the window 32 a predetermined distance. The cutter is coupled to a handle, generally indicated at 34 (FIGS. 12-16) through a coiled drive shaft 36. Actuation of an input device or manual actuator 38 on the handle, which forms part of the deployment mechanism in this embodiment, can activate the drive shaft 36 and cutter, and move the cutter 28 longitudinally over a cam so as to deflect the distal portion and move the cutter 28 out of cutting window 32. Camming of the cutter 28 can cause the distal portion 26 to pivot or deflect relative to the proximal portion 24 so as to deflect and urge the cutter into the tissue in the body lumen.

In some embodiments, the distal portion 26 of the catheter may be moved to an angled or offset configuration from the longitudinal axis of the proximal portion 24 of the catheter and the cutter 28. In some embodiments, the cutter 28 can also be deflected off of the axis of the proximal and/or distal portion of the catheter. Moving the distal portion 26 to an angled/offset position may cause a portion of the catheter to urge against a target tissue, may expose the cutter 28 through the window 32 or both, in various embodiments.

The proximal portion 24 of the catheter body 22 may be relatively flexible and the distal portion 26 may be relatively rigid. Additionally, many embodiments include a flexible distal tip member 42. The flexible proximal portion 24 of the catheter is typically a torque shaft and the distal portion 26 is typically a rigid tubing. The torque shaft 24 facilitates transportation of the catheter body 22 and cutter 28 to the diseased site. The proximal end of the torque shaft 24 is coupled to the handle 34 and the distal end of the torque shaft is attached to the distal, rigid portion 26 of the catheter through the connection assembly 27. The drive shaft 36 is movably positioned within the torque shaft 24 so as to rotate and axially move within the torque shaft 24. The drive shaft 36 and torque shaft 24 are sized to allow relative movement of each shaft without interfering with the movement of the other shaft. The catheter body 22 will have the pushability and torqueability such that torquing and pushing of the proximal end will translate motion to the distal portion 26 of the catheter body 22.

Figure 2:
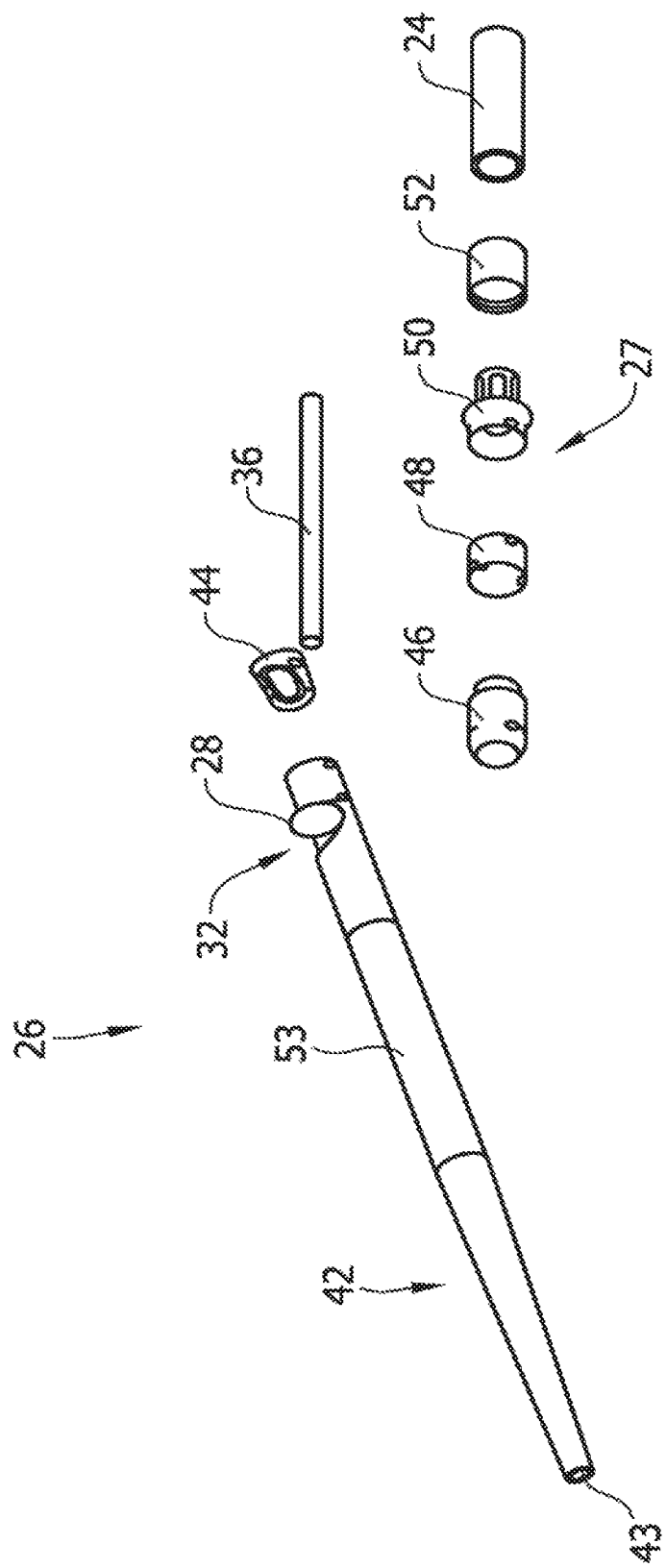
FIG. 2 is an exploded view of an exemplary distal portion of the tissue-removing catheter.

Referring to FIG. 2, the catheter 20 includes the connection assembly 27, rigid housing 26, distal tip member 42 that at least partially defines a collection chamber 53 for storing the severed atheromatous material, and a lumen that can receive the guidewire. The distal tip member 42 can have a distal opening 43 that is sized to allow an imaging guidewire or conventional guidewire (not shown) to be advanced distally through the tip member. In some embodiments, the distal tip member 42 may also include a distal guidewire lumen (not shown) for allowing passage of a guidewire. For example, some embodiments may include a distal guidewire lumen having a length of between about 1.0 cm and about 5.0 cm, and preferably between about 2.0 cm and about 3.0 cm. Such a distal guidewire lumen may be used alone or in conjunction with a proximal guidewire lumen located on another, more proximal, portion of the catheter 20.

A ramp or cam 44 can at least partially fit within the distal portion 26 of the catheter 20. As will be described in detail below, in many embodiments proximal movement of the cutter 28 over the ramp 44, causes the deflection of the distal housing 26 and guides cutter out of cutting window 32. (In other embodiments, a ramp may be used to deflect the distal portion without extending the cutter out of the window.) Attached to the ramp 44 is a housing adaptor 46 that can connect one or more articulation members 48 to the distal tip member 42 to create an axis of rotation of the distal portion 26. The housing adaptor 46 and articulation member 48 allow the distal portion 26 of the catheter to pivot and bias against the body lumen. In the illustrated embodiment there are only one housing adaptor 46 and one articulation member 48, but it should be appreciated that the catheters of the present invention can include, two, three, or more joints (e.g., axis of rotation), if desired. Moreover, the axes of rotation can be parallel or non-parallel with each other.

The catheter 20 can also include a shaft adaptor 50 and collar 52 to couple articulation members 48 to the torque shaft 22. Shaft adaptor 50 can connect the housing to the torque shaft 22 and the collar 52 can be placed over a proximal end of the shaft adaptor and crimped for a secure attachment. It should be appreciated by one of ordinary skill in the art that while one catheter embodiment has the above components that other catheters may include more or fewer of the components described above. For example, some components can be made integral with other components and some components may be left out entirely. For example, instead of having a separate ramp 44, the ramp may be integrated with the distal portion 26 to direct the cutter 28 out of the cutting window 32.

As shown in FIGS. 3-5, the cutter 28 will generally be movable between two or more positions using a deployment mechanism. In the illustrated embodiment, the actuator 38 actuates operation of the deployment mechanism, although in other embodiment, the deployment mechanism may be actuated by other actuators. In the illustrated embodiment, the deployment mechanism allows for the cutter 28 to be moveable to a stowed or neutral position (FIGS. 3A and 3B) in which the cutter stowed in the distal portion 26 of the catheter body 22 and is not exposed through the window 32. In some embodiments, an imaging device (not shown) can be coupled to cutter 28 so as to image the body lumen through cutting window 32 when cutter is in the neutral position. Once the catheter 20 has reached the target site, the cutter 28 can be moved proximally to a cutting position (FIGS. 4A and 4B), in which the cutter 28 extends through the cutting window 32 a distance L1 beyond an outer diameter D of the distal portion 26. In some embodiments, in the cutting position, the cutter 28 will have deflected the distal portion 26 and the cutter's axis of rotation will generally be in line with connection assembly 27 but angled or offset from longitudinal axis of the distal portion of the catheter body 22.

Optionally, in some embodiments, the cutter 28 can be moved to a packing position, in which the cutter is moved distally, beyond the stowed or neutral position, so as to pack the severed tissue into the distal collection chamber 53 (FIGS. 5A and 5B). It should be appreciated however, that while the exemplary embodiment moves the cutter 28 to the above described positions, in other embodiments the cutter can be positioned in other relative positions. For example, instead of having the neutral position distal of the cutting window, the neutral position may be proximal of the window, and the open position may be along the distal end of the cutting window, or the like.

Referring again to FIGS. 4A and 4B, the interaction of the components of the rigid distal portions 26 in one exemplary embodiment will be further described. As shown in FIG. 4B, the cutting window 32 is typically a cutout opening in the distal portion 26. While the size of the cutting window 32 can vary, the cutting window should be long enough to collect tissue and circumferentially wide enough to allow the cutter to move out of the cutting window during cutting, but sized and shaped to not expel emboli into the vasculature. Cams or ramp 44 (shown most clearly in FIG. 4B) can be disposed in the distal portion 26 of the catheter body 22 to guide or otherwise pivot the cutter 28 out of the cutting window 32, from the non-exposed, neutral position (FIG. 3B) to the exposed, cutting position (FIG. 4B) as the cutter 28 is pulled proximally through tensioning of drive shaft 36. This operation is explained in detail below.

Referring to FIGS. 4A and 4B, a joint 49 is located proximal to the cutting window 32 to provide a pivot point for camming of the distal portion 26 relative to the proximal portion 24. The bending at the joint 49 is caused by the interaction of the cams or ramps 44 with cutter 28 and the tensile force provided through drive shaft 36. In the exemplary configuration, the joint 49 includes a housing adaptor 46 that is pivotally coupled to the distal rigid portion 26. As shown in FIGS. 4A and 4B, the resulting pivoting of the rigid distal portion 26 relative to the proximal portion 24 causes a camming effect which urges the distal portion against the body lumen wall without the use of urging means (e.g., a balloon) that is positioned opposite of the cutting window 32. Thus, the overall cross sectional size of the catheter body 22 can be reduced to allow the catheter 20 to access lesions in smaller body lumens. In exemplary embodiments, the distal portion 26 can deflect off of the axis of the proximal portion 24 of the catheter 20 typically between 0° degrees and 30° degrees, usually between 5° degrees and 20° degrees, and most preferably between 5° degrees and 10° degrees. The angle of deflection relates directly to the urge. Urge, however, does not necessarily relate to force but more to the overall profile of the catheter 20. For example, the greater the angle of deflection, the larger the profile and the bigger the lumen that can be treated. The ranges were chosen to allow treatment of vessels ranging from less than 2 mm to greater than 3 mm within the limits of mechanical design of the components. It should be appreciated however, that the angles of deflection will vary depending on the size of the body lumen being treated, the size of the catheter, and the like.

In some embodiments, the deflection of the distal portion 26 of the catheter 20 urges the cutter 28 into the exposed, cutting position (FIG. 4B such that distal advancement of the entire catheter body 22 can move the rotating cutter through the occlusive material. Because the cutter 28 is moved a distance L1 beyond the outer diameter of the distal portion 26 of the catheter 20 and outside of the cutting window 32, the user does not have to invaginate the tissue into the cutting window. In some embodiments, for example, the cutter 28 can be moved between about 0.025 mm and about 1.016 mm, and preferably between about 0.025 mm and about 0.64 mm, beyond the outer dimension of the distal portion 26. It should be appreciated that the cutter excursion directly relates to the depth of cut. The higher the cutter 28 moves out of the cutting window 32 the deeper the cut. The ranges are chosen around efficacy without risk of perforation of the body lumen.

Figure 4C:
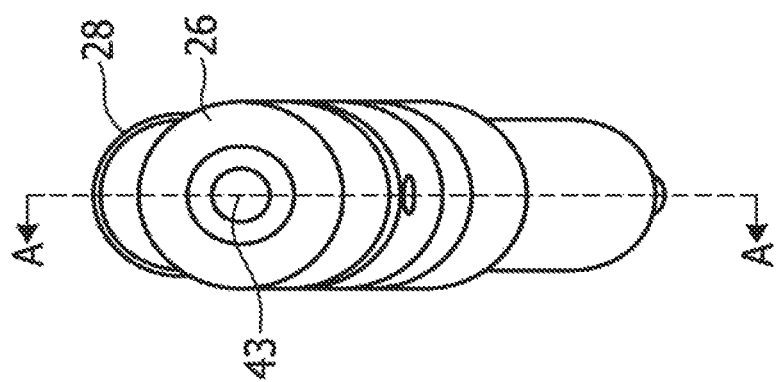
FIGS. 4C and 4D are views of the distal portion of a tissue-removing catheter similar to FIGS. 4A and 4B, where the distal portion has a locking shuttle mechanism.
Figure 4D:
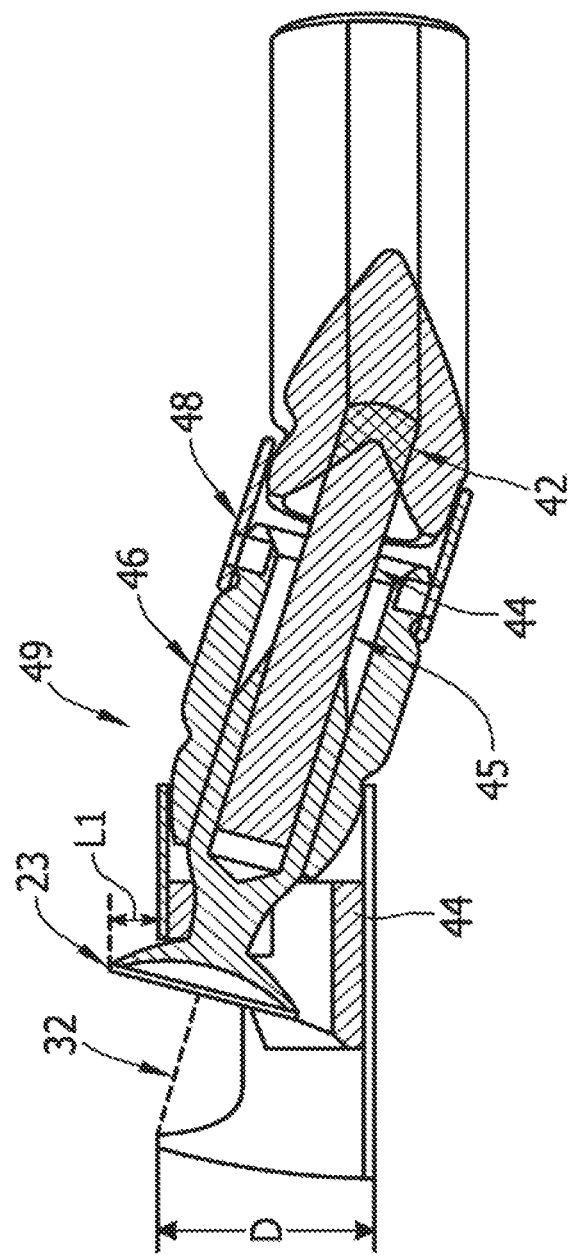

Some embodiments of the catheter 20 include a shuttle mechanism or other similar mechanism for temporarily locking the catheter in the cutting position. FIGS. 3C and 3D illustrate such an embodiment in the neutral, non-cutting position. Such embodiments generally include a shuttle member 45 and a shuttle stop member 42. The shuttle stop member 42 is typically disposed at an angle, relative to a longitudinal axis through the catheter. FIGS. 4C and 4D show the same embodiment in the cutting position. When the cutter 28 is moved into the cutting position in such embodiments, the shuttle member 45 falls into the shuttle stop member 42 and thus locks the cutter 28 in the cutting position. To unlock the cutter 28, the cutter may be advanced forward, distally, to release the shuttle member 45 from the shuttle stop member 42.

Some embodiments including a shuttle mechanism will also include two joints in the catheter body 22. Thus, catheter body 22 will include the distal portion 26, the proximal portion 24 and a middle portion. When shuttle mechanism is activated to expose cutter 28 through window 32, the middle portion may orient itself at an angle, relative to the proximal and distal portions, thus allowing cutter to be urged towards a side of a lumen. Such a two-jointed configuration may provide enhanced performance of the catheter 20 by providing enhanced contact of the cutter 28 with material to be debulked from a body lumen.

Pushing the entire catheter 20 across a lesion removes all or a portion of the lesion from the body lumen. Severed tissue from the lesion is collected by directing the removed tissue into the collection chamber 53 in the tip member 42 via the cutter 28. Once the catheter 20 and cutter 28 have moved through the lesion, the cutter 28 can be advanced distally to "part off position" the lesion. During "parting off", the cutter is moved distally from the cutting position back into the cutting window 32 (FIG. 5B) and to its neutral or stowed position. The collection chamber 53 of the tip member 42 acts as a receptacle for the severed material, to prevent the severed occlusive material from entering the body lumen and possibly causing downstream occlusions. After "parting off", the cutter 28 can be moved distally to a packing position, in which the cutter moves distally within the collection chamber 53 to pack the severed tissue into collection chamber 53 (FIG. 3B). Typically, the collection chamber 53 will be large enough to allow multiple cuts to be collected before the catjeter 20 has to be removed from the body lumen. When the collection chamber 53 is full, or at the user's discretion, the catheter 20 can be removed, emptied and reinserted over the guidewire.

In various embodiments, enhancements to the collection chamber 53 may be included. For example, in some embodiments the collection chamber 53 may be configured to be partially or completely translucent or radiolucent and a portion of the catheter 20 surrounding or adjacent to the window 32 will be radiopaque. This combination of radiolucent collection chamber 53 and radiopaque material adjacent window 32 will enhance the ability of a user to determine how full the collection chamber 53 is, because the fullness of the collection chamber will be directly related to the distance the cutter 28 can advance forward into the collection chamber 53. By facilitating the assessment of collection chamber filling, these embodiments will reduce the need for manually withdrawing the catheter to examine the collection chamber 53.

Figure 6:
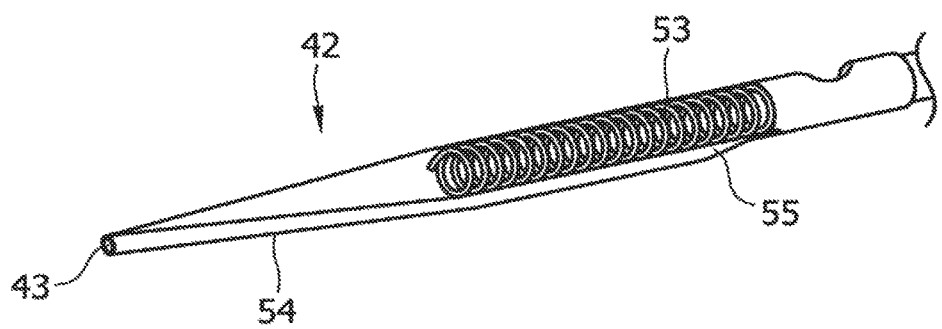
FIGS. 6 to 8 illustrate a monorail delivery system of the present invention.
Figure 7:
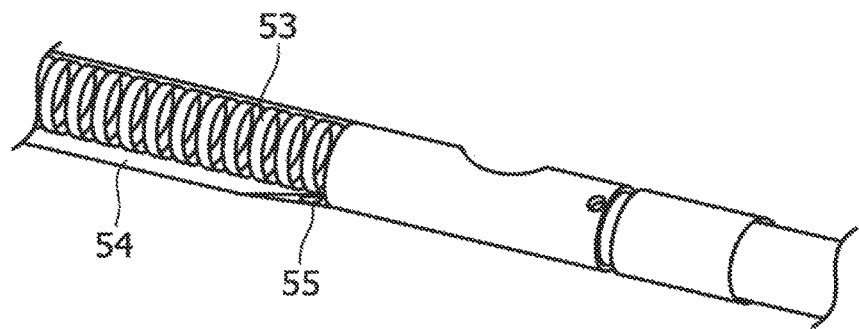
Figure 8:
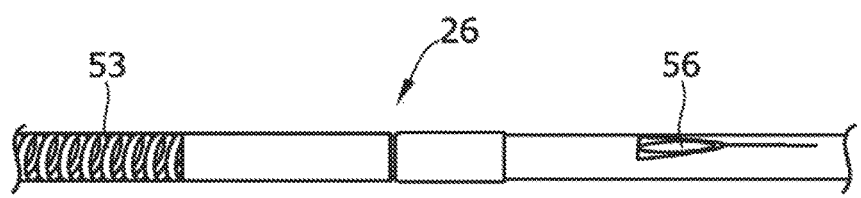

FIGS. 6 through 8 illustrate one exemplary monorail delivery system to assist in positioning the cutter 28 at the target site. For example, tip member 42 of the catheter can include a lumen 54 having a distal opening 43 and a proximal opening 55 that is sized to receive a guidewire, having a diameter of about 0.014 in., about 0.018 in., about 0.032 in. or any other suitable diameter.

The catheters 20 can include radiopaque markers so as to allow the user to track the position of the catheter tinder fluoroscopy. For example, as already described, a point or area around or adjacent to the window 32 may be made radiopaque. In other embodiments, the rigid distal portion 26 can be radiopaque and radiopaque markers can be disposed on the flexible shaft 36. Typically, the markers 59 will be disposed along the top, proximal to the cutting window 32, and on the bottom of the catheter 20 to let the user know the position of the cutter and cutting window relative to the target site. If desired, the top and bottom markers can be different shaped so as to inform the user of the relative orientation of the catheter 20 in the body lumen. Because the guidewire will form a helix in its transition from lumen 56 to tip member lumen 54, the user will be able to view the top and bottom radiopaque markers 59 without interference from the guidewire. Some embodiments of the catheter 20 can also include a radiopaque cutter stop 61 (FIG. 3B) that is crimped to driveshaft 36 proximal of the cutter that moves with the cutter so as to let the user know when the cutter 28 is in the open position.

FIGS. 9A through 11D show some exemplary embodiments of the cutter 28. The distal portion 60 of the rotatable cutter 28 can include a serrated knife edge 62 or a smooth knife edge 64 and a curved or scooped distal surface 66. The distal portion 60 may have any suitable diameter or height. In some embodiments, for example, the diameter across the distal portion 60 may be between about 0.1 cm and about 0.2 cm. A proximal portion 68 of the cutter 28 can include a channel 70 that can be coupled to the drive shaft 36 that rotates the cutter. As shown in FIGS. 10A-10C, some embodiments of the cutters 28 can include a bulge or bump 69 that is provided to interact with a stent so as to reduce the interaction of the cutting edge with the stent. In any of the foregoing embodiments, it may be advantageous to construct a serrated knife edge 62, a smooth knife edge 64, or a scooped distal surface 66 out of tungsten carbide.

Figure 11D:
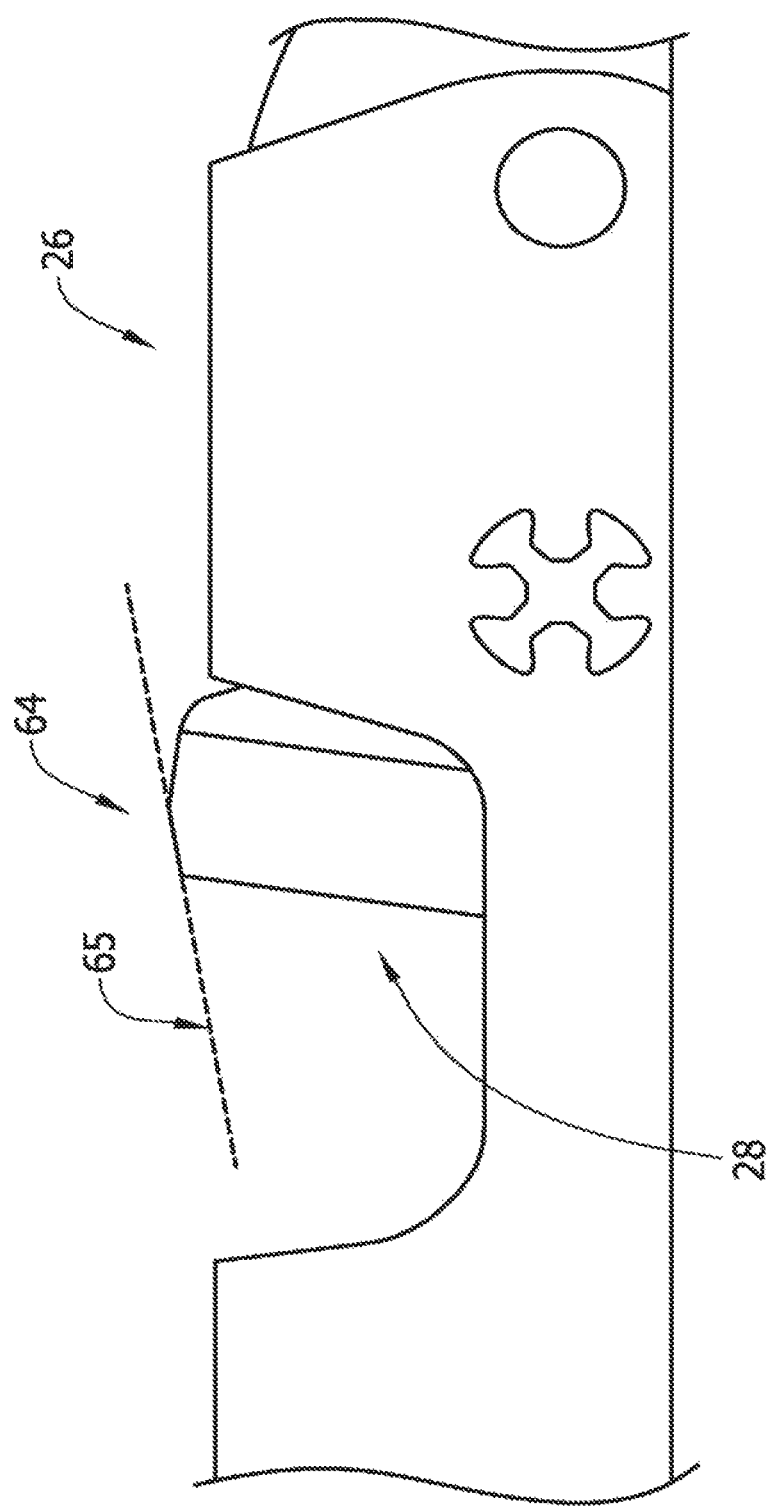
FIG. 11D is a side view of another embodiment of a tissue-removing element, shown partially within a catheter body.
Figure 12:
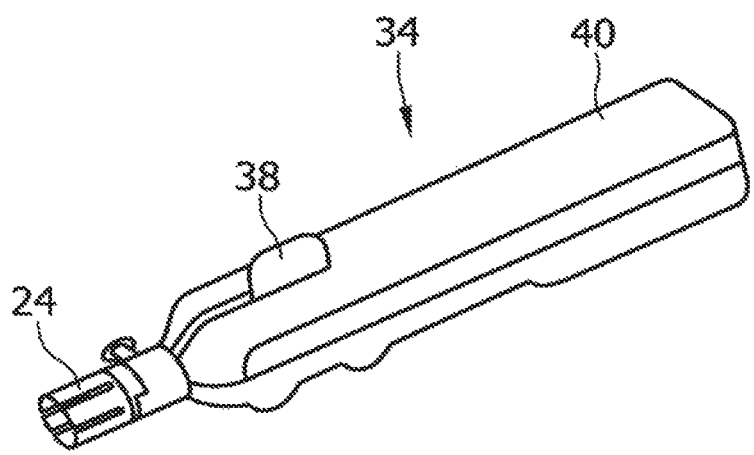
FIG. 12 is a perspective of a first embodiment of a handle for the tissue-removing catheter, including a first embodiment of an operational control mechanism.
Figure 13:
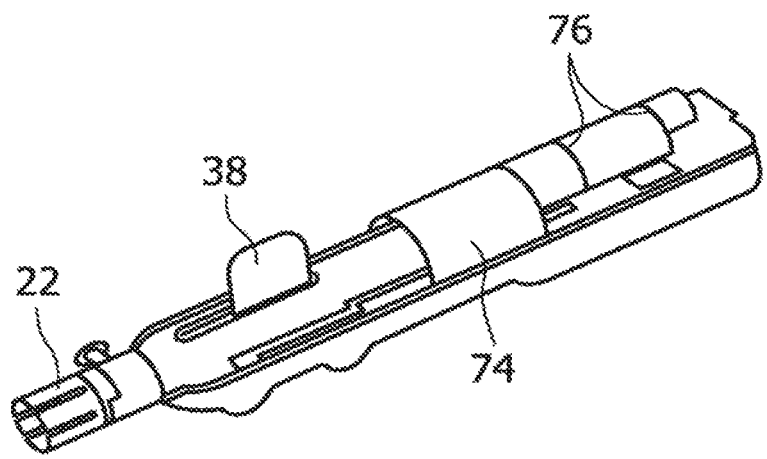
FIG. 13 is similar to FIG. 12 with a cover of the handle removed.
Figure 14:
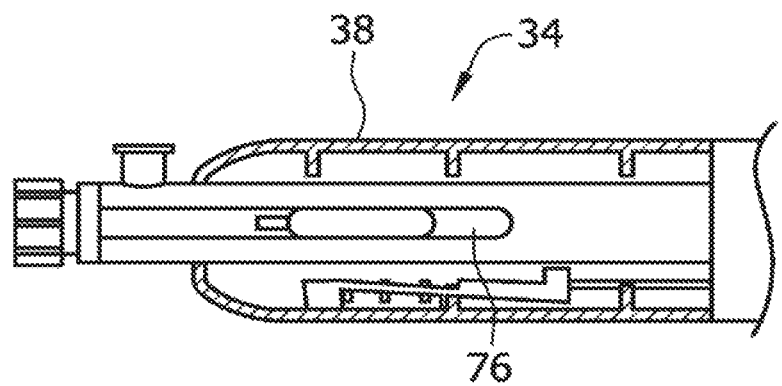
FIGS. 14 to 16 are top, partial section views of the handle illustrating three positions of a lever of the handle for operating the tissue-removing element.
Figure 15:
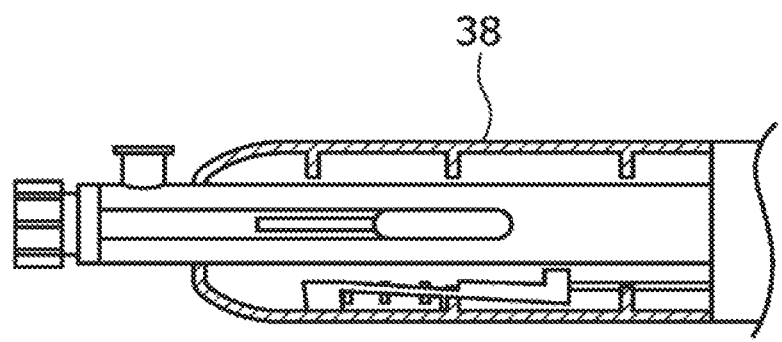

Another embodiment of a cutter 28 suitable for use in the present invention is shown in side view within a distal portion 26 in FIG. 11D. In this embodiment, the cutter 28 has a beveled edge 64, made of tungsten carbide, stainless steel, titanium or any other suitable material. The beveled edge 64 is angled inward, toward the axis of rotation (or center) of the cutter 28, creating a "negative angle of attack" 65 for the cutter 28. Such a negative angle of attack may be advantageous in many settings, when one or more layers of material are desired to be debulked from a body lumen without damaging underlying layers of tissue. Occlusive material to be removed from a vessel typically has low compliance and the media of the vessel (ideally to be preserved) has higher compliance. A cutter 28 having a negative angle of attack may be employed to efficiently cut through material of low compliance, while not cutting through media of high compliance, by allowing the high-compliance to stretch over the beveled surface of cutter 28.

Referring to FIGS. 12 through 16, one embodiment of the handle 34 will now be described in detail. The handle 34 includes a housing 40 that is sized and shaped to be held in a hand of the user. An electric motor 74 (e.g., a DC motor) is contained in the housing 40, along with a power source 76 (e.g., a battery or other source of DC power) electrically connected to the motor for powering the motor. The drive shaft 36 is operatively coupled to the motor 74 when the catheter 20 is connected to the handle 34 for driving rotation of the drive shaft and the cutter 28. In some embodiments, the motor 74 can rotate drive shaft 36 between 1,000 rpm and 10,000 rpm or more, if desired. The manual actuator 38

Figure 16:
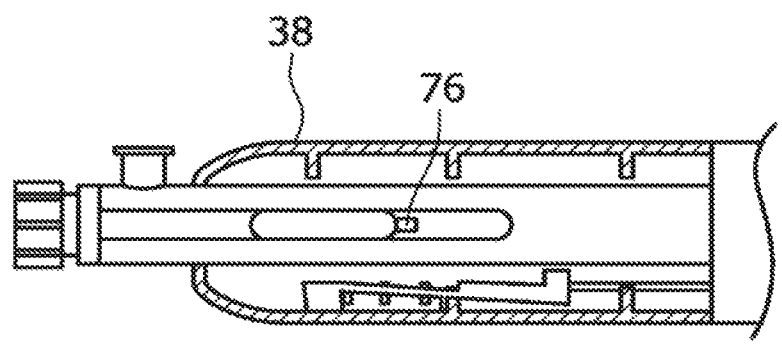

(e.g., the lever, as illustrated) on the exterior of the housing 40 allows the user to control operations of the catheter 20. For example, in the illustrated embodiment the lever 38 is axially moveable relative to the housing 40. In particular, the lever 38 is movable to a neutral position (shown in FIG. 14), whereby the cutter 28 is in its non-exposed, neutral position (FIG. 3D). To expose the cutter 28 and activate the motor 74 to drive rotation of the cutter, the lever 38 is moved proximally from the neutral position to a proximal position (broadly, a cutting position of the lever; see FIG. 15) to move the cutter proximally and out of cutting window 32 (FIG. 4B) to its cutting position and simultaneously activate the motor 74. For example, proximal movement of the lever 38 to the proximal position may actuate (e.g., depress) an electrical switch 78 that electrically connects the power source 76 to the motor 74. To part off tissue, the lever 38 is moved distally from the proximal position, back to its neutral position (FIG. 14), whereby the cutter is moved distally back into the distal portion (FIG. 3D), and the electrical switch 78 is released (i.e., opened) so as to deactivate the electric motor 74. To pack the removed tissue in the collection chamber 53 in the distal tip member 42, the lever 38 is moved distally from the neutral position to a distal position (broadly, a packing position of the lever; FIG. 16) to push the cutter 28 into its packing position. It should be appreciated, while the figures illustrate the use of an lever 38 or thumb switch, the present invention can use other types of actuators, such as labeled buttons (e.g., close window, debulk tissue, and pack), or the like.

Figure 17:
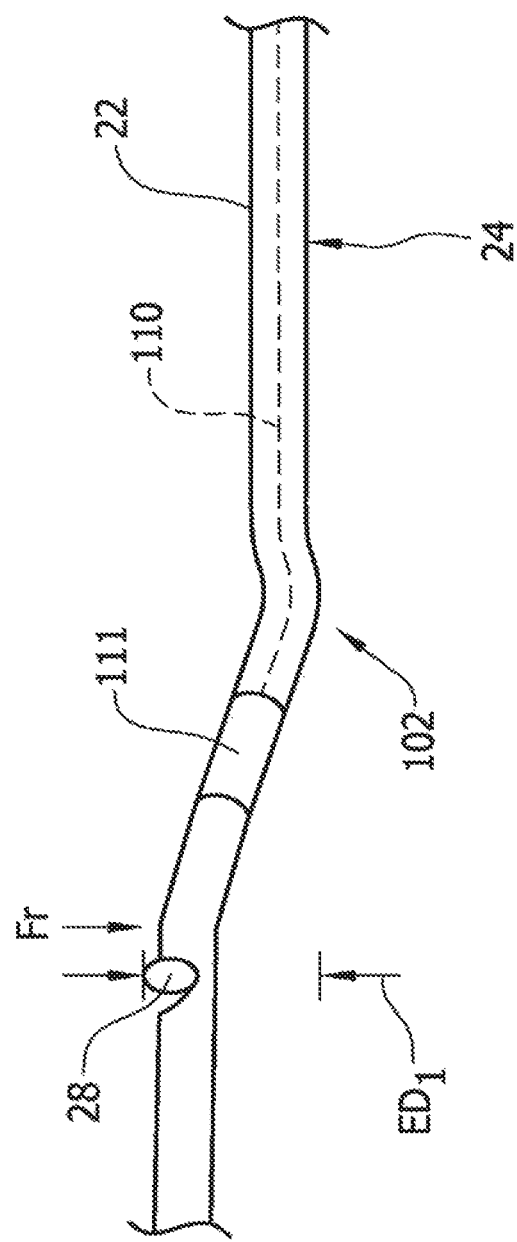
FIG. 17 is a schematic of the tissue-removing catheter showing a jogged portion of the catheter.

Referring to FIGS. 1 and 17, the catheter body 22 has a jogged portion, generally indicated at 102, that is generally adjacent a distal end of the proximal portion 24. The catheter body 22 juts radially outward immediately distal of the jogged portion 102. As a non-limiting example, the jogged portion 102 may have one or more curved sections for generally abruptly changing the direction that the catheter body 22 extends. A torque tube (not shown) of the catheter body 22 may be preformed with this shape to define the jogged portion 102 of the catheter. As shown in FIG. 17, the jogged portion 102 gives the catheter body 22 an effective diameter ED1 at the cutter 28. Referring still to FIG. 17, the catheter 20, at the jogged portion 102, may elastically deform to a relatively more linear configuration (i.e., flatten out to a smaller effective diameter ED) when a transverse force (e.g., force FT) is applied to the catheter body 22 adjacent the cutter 28. Accordingly, when the catheter body 22 is received in a body lumen BL (see FIG. 18) having an inner diameter less than the effective diameter ED1 of the catheter at the jogged portion 102, the jogged portion elastically deforms (e.g., flattens out) and the cutter 28 (when deployed) is pushed against a portion of the wall of the body lumen (e.g., a lesion site) that generally diametrically opposes the portion of the body lumen wall that is contacted by the jogged portion.

Figure 18:
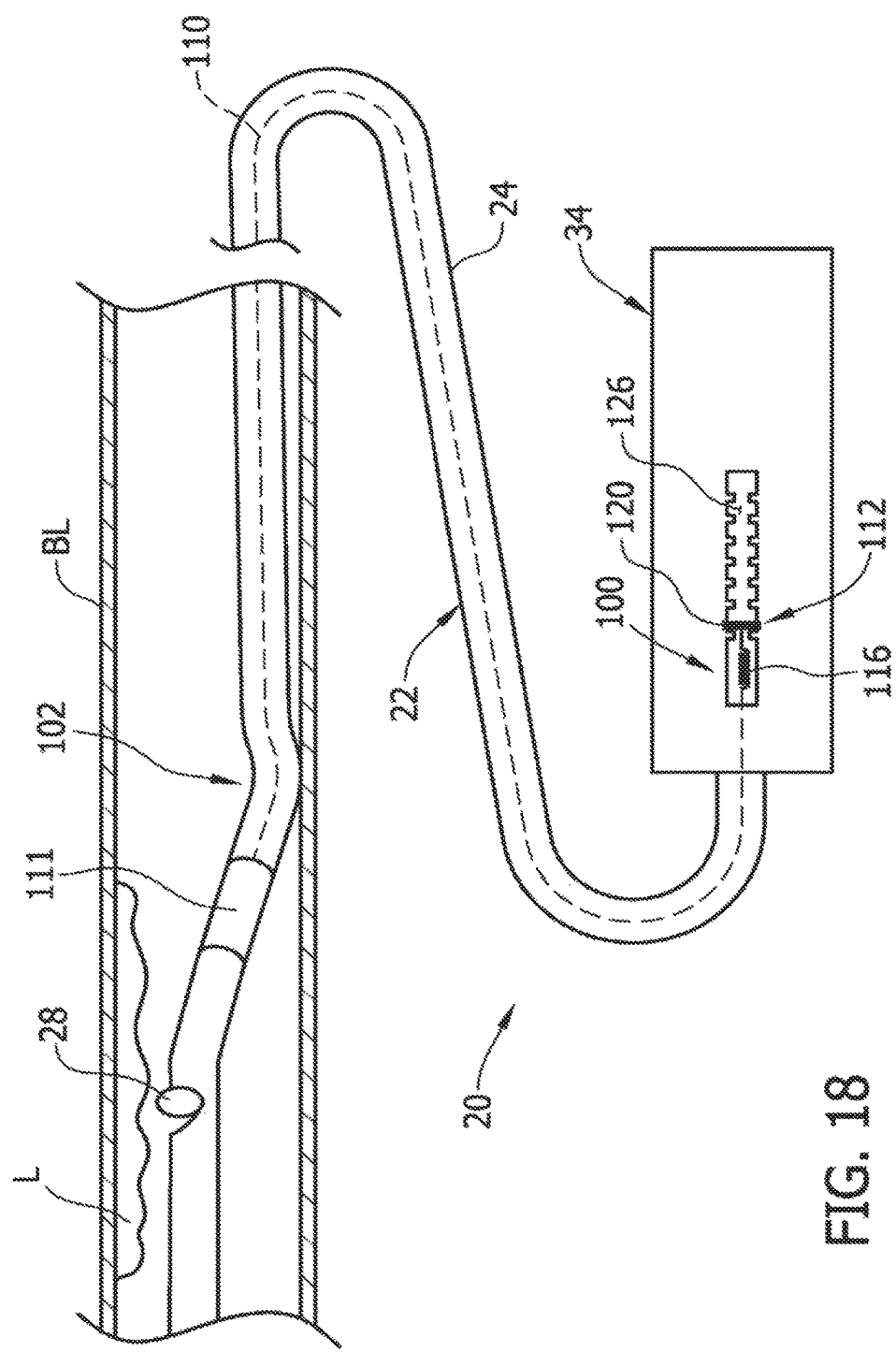
FIG. 18 is a schematic of the tissue-removing catheter showing a first embodiment of an urging mechanism, the urging mechanism being in an active state.
Figure 19:
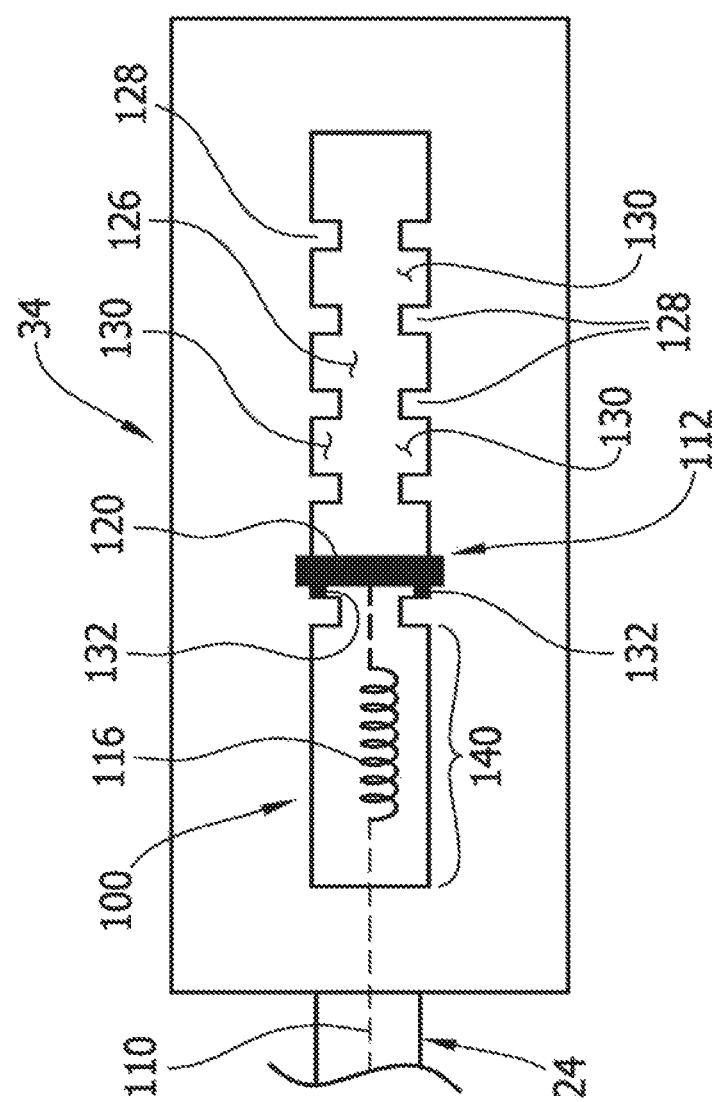
FIG. 19 is an enlarged schematic of the handle and urging mechanism of FIG. 18.
Figure 20:
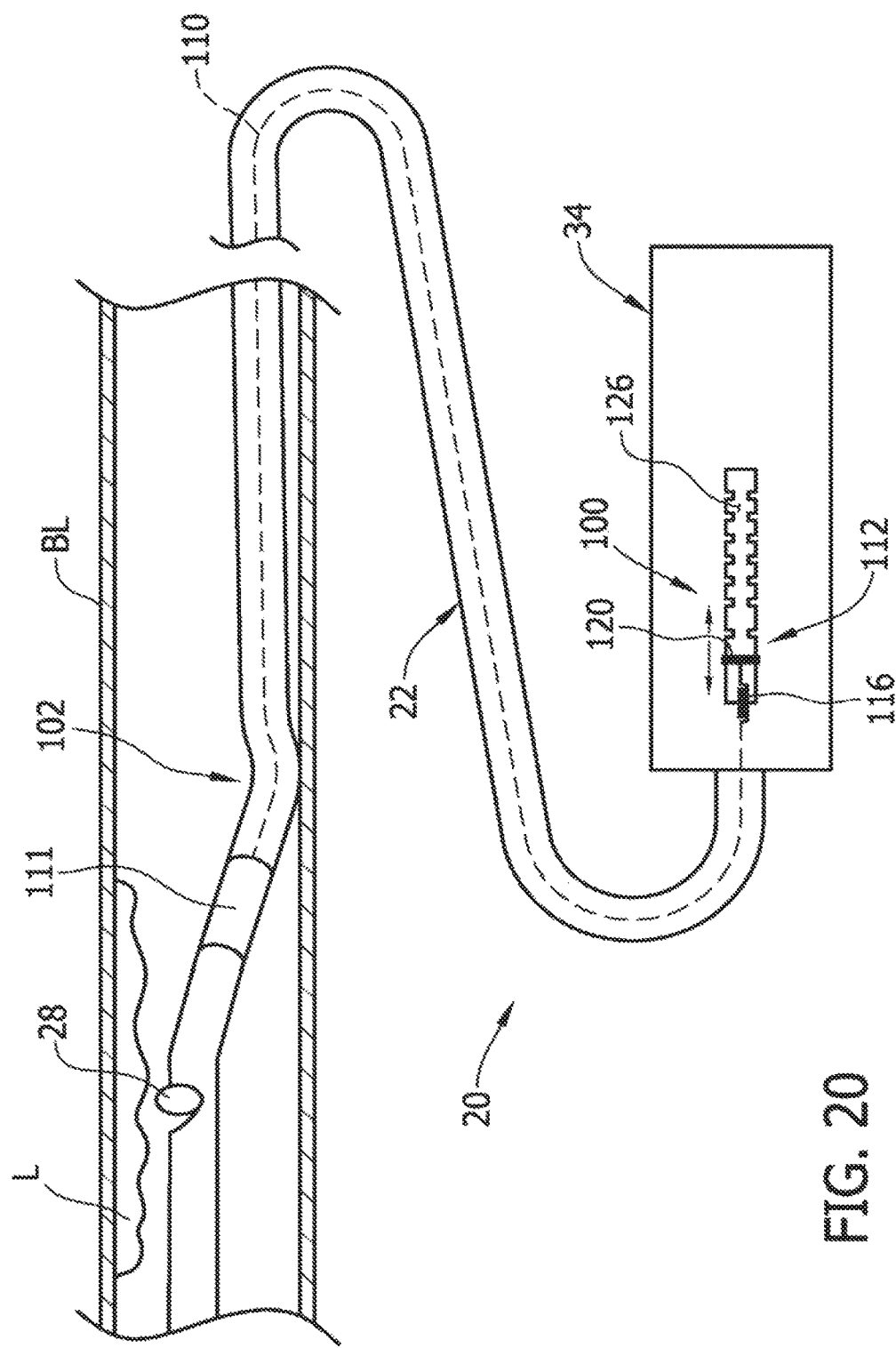
FIG. 20 is similar to FIG. 18, with the urging mechanism in a relaxed state.

Referring now to FIGS. 18-20, a first embodiment of an urging mechanism for adjusting the force by which the cutter 28 is urged against a wall of the body lumen (e.g., toward the lesion site) to enhance treatment is generally indicated at 100. The urging mechanism 100 is used to selectively apply and adjust an axial compressive load applied to the catheter body 22, which in turn adjusts the bending stiffness of the catheter body at the jogged portion 102, to allow for adjustment of the urge force imparted against the body lumen wall by the jogged portion 102. The urging mechanism 100 includes an elongate tension member 110 extending along the catheter body 22 (e.g., extending within a longitudinal lumen of the catheter body). In one non-limiting example, the tension member 110 comprises a flexible cable or wire, such as a stainless steel wire, that is generally not elongated during use (i.e., generally non-deformable along its length during use) and is movable longitudinally with respect to the catheter body 22. The tension member 110 may be of other types and configurations. A distal portion of the tension member 110 is fixedly secured to the catheter body 22 at a location distal of the jogged portion 102. For example, the distal portion of the tension member 110 may be secured to a fixed connector 111 that is fixedly secured to the catheter body 22. A proximal portion of the tension member 110 is secured to a tension-adjusting device, generally indicated at 112. In the illustrated embodiment, the tension-adjusting device 112 comprises an elastic tension member 116 secured to the proximal end of the tension member 110, and a load actuator 120 for selectively applying a tensile load to the elastic tension member. The elastic tension member 116 is located in the handle 34, and the load actuator 120 is accessible by the user when holding the handle. In one non-limiting example, the elastic tension member 116 may comprise a tension spring (also known as an extension spring) that is elastically deformable (i.e., elastically elongatable) along its longitudinal axis when a tensile load is applied thereto. In the illustrated embodiment, the longitudinal axis of the tension spring 116 is generally coaxial or generally parallel to the longitudinal axis of the catheter body 22 at the proximal end of the catheter body.

In one non-limiting example, the load actuator 120 is fixedly secured to the tension spring 116 adjacent the proximal end of the spring for use in selectively applying a tensile load to the spring, and in turn, selectively applying a tensile load to the tension member 110, which imparts an axial compressive load on the catheter body 22. The load actuator 120 comprises a lever, knob, or some other manual actuator for applying a tensile load adjacent the proximal end of the tension spring 116 so that the spring elastically elongates along its longitudinal axis. For example, where the load actuator 120 comprises a lever, such as a thumb lever, movement of the lever proximally relative to the handle 34 applies a tensile load to the tension spring 116. In the illustrated embodiment, the load actuator 120 forms part of a detent mechanism. The detent mechanism allows for selectively locking and unlocking the position of the load actuator 120 relative to the handle 34, which in turn, allows for selective, incremental adjustment (i.e., increasing and decreasing adjustment) of the tensile load applied to the tension spring 116. As shown best in FIG. 19, the detent mechanism include a slot-shaped track 126 having teeth 128 spaced apart from one another along the length of the track to define a plurality of transverse slots 130, and a resiliently deformable detent 132 (i.e., a catch) on the load actuator 120 that is selectively receivable in and removable from the transverse slots because it is capable of resiliently deformable as it enters and exits the slots. The detent mechanism may be of other types and configurations without departing from the scope of the present invention.

In one embodiment (FIGS. 18-20), the urging mechanism 100 is configured so that when the spring 116 of the urging mechanism is in its biased, relaxed state (FIG. 20), only the jogged portion 102 of the catheter body 22 applies the urge force to the wall of the body lumen BL. That is, the urging mechanism 100 is capable of applying an axial compressive load to the catheter body 22 only when the urging mechanism is in an active state (i.e., only when the load actuator 120 is applying a tensile load to the spring 116 and the tension member 110), as shown in FIGS. 18 and 19. In one non-limiting example, a distal portion 140 (FIG. 20) of the track 126 allows the actuator 120 and the spring 116 to slide freely in at least the distal direction as the jogged portion 102 flattens out (i.e., when a suitable transverse force $F_T$ is applied to the catheter body 22 adjacent the cutter 28). Thus, only the resiliently deflectable jogged portion 102 applies the urge force to the wall of the body lumen BL when the urging mechanism 100 is in a non-active state.

Referring to FIGS. 18 and 19, when the urging mechanism 100 is in an active state (e.g., when a tensile load is applied to the spring 116, and the tension member 110, using the actuator 120), both the jogged portion 102 and the spring act in series to apply the urge force to the wall of the body lumen BL. In particular, applying tension to the tension member 110 imparts an axial compressive load to the catheter body 22, which in turn increases the bending stiffness of the catheter body, particularly at the jogged portion 102. Increasing the bending stiffness at the jogged portion 102 increases the urge force applied to the wall of the body lumen BL.

It is understood that in at least one embodiment, the jogged portion 102 may not act as a spring and/or may be omitted from the catheter 20, whereby only the urging mechanism 100 causes the catheter body 22 to apply the urge force to the body lumen wall. In such an embodiment, the catheter body 22 may take on the shape of the jogged portion 102 (or another suitable shape) when the urging mechanism 100 is applying a compressive load to the catheter body. In the illustrated embodiment, the jogged portion 102 and/or the urging mechanism 100 are configured so that application of tensile load to spring 116, which imparts compressive load to the catheter body 22, does not substantially change the shape of the catheter, particularly the shape of the jogged portion. As set forth above, the tensile load applied to the tension member 110 by the spring 116 is selectively adjustable using the detent mechanism. In particular, in the illustrated embodiment moving the actuator 120 proximally increase the tensile load on the tension member 110, which causes the catheter body 22 to apply a greater urge force to the body lumen wall due to the increase in bending stiffness at the jogged portion, as compared to urge force applied via only the jogged portion 102, as the cutter 28 engages the lesion L. By allowing a user to adjust the urge force applied against a body lumen wall, the user can better control the cut depth as the cutter 28 passes through the lesion L, since the cut depth may be dependent, at least in part, on the urge force applied against the body lumen wall. Moreover, an adjustable urge force using the urging mechanism 100 may allow for a more consistent urge force to be applied to a broader range of body lumen diameters, as compared to using solely the jogged portion 102 to apply the urge force, because the urge force can be adjusted based on a change in the body lumen diameter.

Indicia or other indication markings may be provided on the handle 34 to indicate a relative amount of urge force being applied at each incremental location of the actuator 120 along the track 126. Alternatively, or in addition, indicia or other indication markings on the handle 34 may inform the user of where the actuator 120 should be positioned in the track 126 based on the diameter of the body lumen BL in order to apply a consistent urge force to the lesion L irrespective of the diameter of the body lumen.

Figure 21:
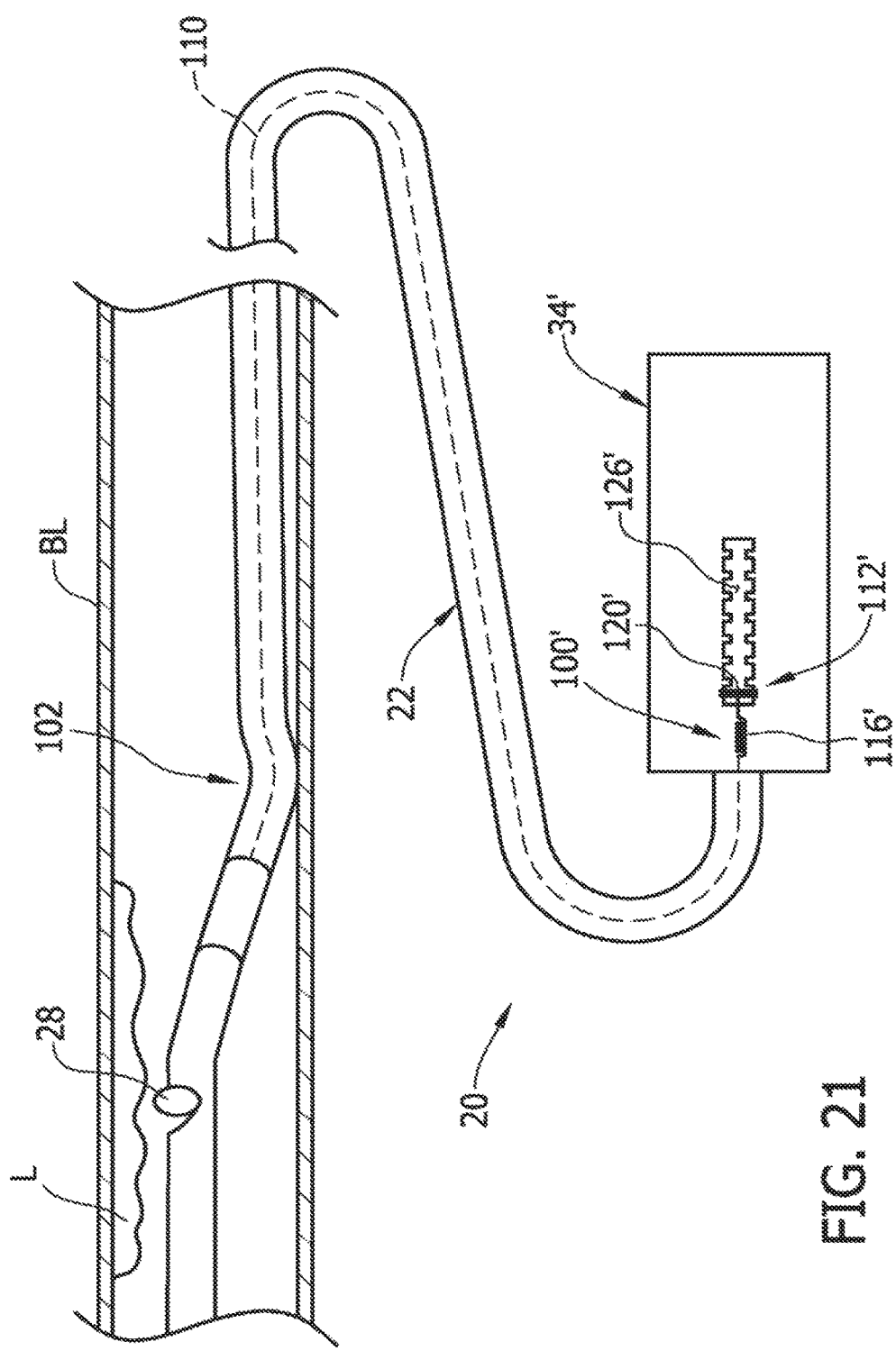
FIG. 21 is a schematic of a tissue-removing catheter including an alternative example of the urging mechanism embodiment of FIGS. 18-20.

In another embodiment, the urging mechanism 100 may always be in an active state. For example, as illustrated in FIG. 21, even when the tension spring 116 is in its relaxed, unloaded state, if the catheter body 22 adjacent the cutter 28 flattens out in the body lumen BL, then a tensile force is applied to the spring at its distal end and the spring elongates, which in turn, increases the urge force applied to the body lumen wall by the jogged portion 102. This is because unlike the prior embodiment, the tension spring 116 in the present catheter is not allowed to slide freely in at least the distal direction as the jogged portion 102 flattens out (i.e., when a suitable transverse force $F_T$ is applied to the catheter body 22 adjacent the cutter 28). Therefore, a tensile load will be applied to the tension member 110, and a compressive load to the catheter body 22, if the jogged portion 102 flattens out.

Figure 22:
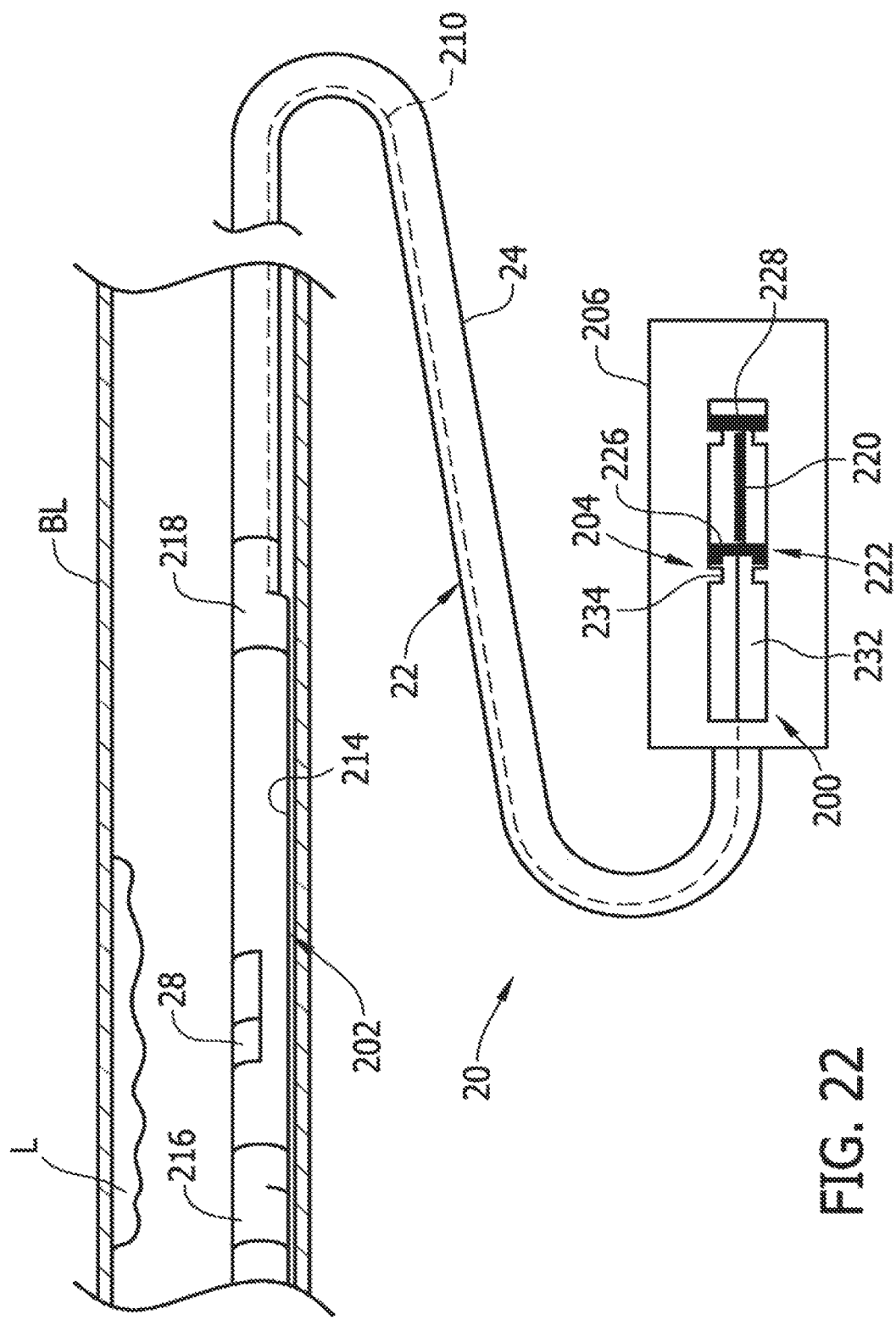
FIG. 22 is a schematic of a tissue-removing catheter including a second embodiment of the urging mechanism, the urging mechanism in a relaxed state.
Figure 23:
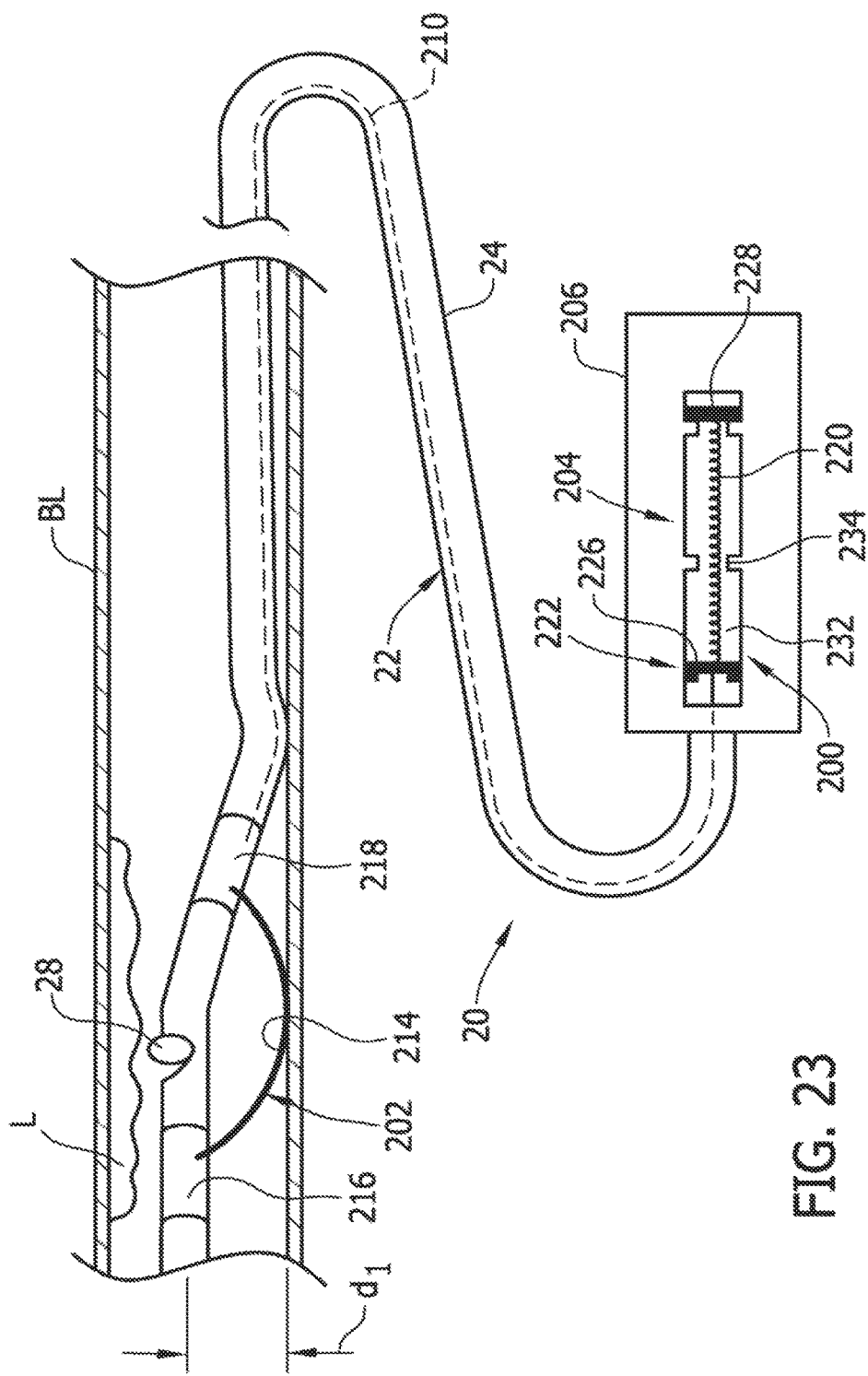
FIG. 23 is similar to FIG. 22, with the urging mechanism in an active state.

Referring to FIGS. 22 and 23, a second embodiment of an urging mechanism for selectively applying an urge force to urge the cutter 28 against a wall of the body lumen (e.g., toward the lesion site) to enhance treatment is generally indicated at 200. This urging mechanism 200 can be used with the catheter illustrated in FIGS. 1 and 17-20, in lieu of the first embodiment of the urging mechanism. As such, FIGS. 22 and 23 illustrate the urging mechanism 200 as being part of the catheter illustrated in FIGS. 1 and 17-20, with like components indicated by corresponding reference numerals. It is understood that the urging mechanism 200 may be used with other types of tissue-removing catheters without departing from the scope of the present invention.

Referring still to FIGS. 22 and 23, the urging mechanism 200 includes a deflection device, generally indicated at 202, adjacent the distal end of the proximal portion 24 of the catheter body 22, and a deflection-actuating device, generally indicated at 204, associated with a handle 206. The urging mechanism 200 also includes an elongate compression-transmitting component (e.g., elongate push member) 210 that is movable longitudinally with respect to the catheter body 22 and operatively connects the deflection device 202 and the deflection-actuating device 204 for transmitting compressive force (e.g., push force) to the deflection device when the deflection-actuating device is in an active state (as shown in FIG. 23). As explained in more detail below, when activated the deflection device 202 urges a portion of the catheter body 22 diametrically opposing the deflection device toward the wall of the body lumen BL (i.e., toward the lesion site). Moreover, in at least one example the deflection-actuating device 204 provides a counterbalance to the urge force applied by the deflection device 202 so that when the deflection device applies a substantially constant urge force across a broad range of body lumen inner diameters.

In the illustrated embodiment, the deflection device 202 comprises a deflector 214 secured to the catheter body 22 via a fixed connector 216 and a longitudinally translatable connector 218 that is spaced apart from the fixed connector along the catheter body. In the illustrated embodiment, the longitudinally translatable connector 218 is proximal of the cutter 28, and the fixed connector 216 is distal of the cutter. A proximal end portion of the deflector 214 is secured to the longitudinally translatable connector 218, and a distal end portion of the deflector is secured to the fixed connector 216. As such, the deflection device 202 is located adjacent to cutter 28 and generally diametrically opposes the cutter, relative to the catheter body 22, although the deflection device may be located elsewhere on the catheter body. One or both of the connectors 216, 218 may comprise a collar or sleeve that is fitted over the catheter body 22, or located inside the catheter body (e.g., fitted over the torque tube). The connectors 216, 218 may be of other types and configurations without departing from the scope of the present invention.

The deflector 214 is configurable between a non-deployed or stowed configuration (FIG. 22), in which the deflector does not impart an urge force to the body lumen wall, and a deployed configuration (FIG. 23), in which the deflector imparts an urge force to body lumen wall, which in turn urges the cutter 28 toward the lesion site. As explained below, the compression-transmitting member 210 selectively imparts longitudinal movement (e.g., sliding movement) of the longitudinally translatable connector 218 relative to the catheter body 22 and the fixed connector 216 to deploy the deflector 214. In its non-deployed configuration, the deflector 214 has a low profile, and may be generally linear and generally parallel to the longitudinal axis of the catheter body 22. In its deployed configuration, the deflector 214 extends a transverse distance $d_1$ (FIG. 23) from the longitudinal axis of the catheter body to apply an urge force against the body lumen wall and urge the cutter toward the lesion L. As explained in more detail below, the longitudinally translatable connector 218 allows the deflector 214 to be resiliently deflectable inwardly toward the longitudinal axis of the catheter body 22 to thereby decrease the transverse distance between the longitudinal axis of the catheter body and the deflector in response to a transverse force applied thereto by the body lumen wall. In the illustrated embodiment, the deflector 214 comprises one or more generally flexible elongate members that buckle (e.g., bend) into a generally arcuate profile when the longitudinally translatable connector 218 is moved longitudinally relative to the catheter body 22 and the fixed connector 216. The deflector 214 may be formed, at least in part, from a shape memory material (e.g., nitinol), such that the deflector is resiliently biased in either the non-deployed, linear configuration or the deployed, arcuate configuration.

Referring still to FIGS. 22 and 23, the deflection-actuating device 204 includes an elastically compressible component 220 secured to the proximal end of the compression-transmitting member 210, and a load actuator, generally indicated at 222, for selectively locking and unlocking the elastically compressible component to selectively configure the deflector between its respective non-deployed and deployed configurations. In one embodiment, the elastically compression component 220 comprises a compression spring that is expandable distally relative to the handle. For example, in the illustrated embodiment a proximal portion of the compression-transmitting member 210 and a distal portion of the compression spring 220 are secured to a movable connector 226 of the load actuator 222 that is selectively movable relative to the handle 206, and a proximal portion of the compression spring 220 is secured to a non-movable connector 228 (i.e., the proximal portion of the compression spring is fixed relative to the handle 206). The movable connector 226 is received in a track 232 and releasably lockable relative to the handle 206, such as by teeth 234 on the track. In an initial state when the deflector 214 is in its non-deployed configuration and the movable connector 226 is locked (FIG. 22), the compression spring 220 may be pre-loaded with an initial stored energy that is less than the maximum potential energy for the spring. For example, the compression spring 220 may be compressed from about 15% to about 85% of its maximum length. Upon unlocking the movable connector 226, the compression spring 220 expands axially to move the compression-transmitting member 210 distally, which imparts distal movement of the longitudinally movable connector 218 to facilitate deployment of the deflector 214.

The compression spring 220 applies a suitable force to the deflector 214 so that the deflector applies a suitable urge force to the body lumen wall to urge the cutter 28 toward the lesion L. In one example, where the deflector 214 is formed from nitinol or other shape-memory material or otherwise formed to be biased to its linear (i.e., flat) configuration, the compression spring 220 also applies a suitable counterforce to the deflector to both overcome the bias of the deflector and to apply a suitable urge force to the body lumen BL when the deflector engages the body lumen wall.

In one embodiment, the compression spring 220 or other elastically compressible component has a relatively small spring constant, which may be from about 0.02 lb/in to about 0.2 lb/in, or from about 0.04 lb/in to about 0.08 lb/in, or about 0.06 lb/in. Because the compression spring 220 has a relatively small spring constant, when the deflector 214 flattens out (i.e., takes on a more linear shape), such as when the catheter 20 enters a smaller diameter body lumen portion, the compression spring compresses a relatively small amount, which causes to a relatively small change in force applied to the deflector because of the relatively small spring constant. Thus, the urge force applied by the deflector 214 to urge the cutter 28 toward the lesion remains substantially constant when the transverse distance $d_1$ between the longitudinal axis of the catheter body 22 and the deflector increases and decreases as the catheter moves through portions of the body lumen having different inner diameters. As used herein, to apply a "substantially constant urge force" means that when the catheter body moves from a 7 mm inner diameter body lumen portion to a 3 mm inner diameter body lumen portion, the transverse urge force applied to the body lumen wall increases less than 0.03 lb from the initial transverse urge force. In one example, the transverse urge force applied to the body lumen wall increases from about 0.01 lb to about 0.002 lb from the initial transverse urge force. Moreover, because of the configuration of the deflection device 202 (e.g., the deflector 214 being fixed to the body 222 at one end and axially slidable at the opposite end to impart force to the spring 220) the urge force applied by the deflector 214 against the body lumen wall is generally not directly proportional to the transverse distance $d_1$ between the longitudinal axis of the catheter body 22 and the deflector. Other ways of applying a substantially constant urge force against the body lumen wall as the catheter moves through portions of the body lumen having different inner diameters do not depart from the scope of the present invention.

Because of the relatively small spring constant, it takes relatively considerable displacement of the spring 220 to apply the necessary force to move the longitudinally translatable connector 218 and deploy the deflector 214 and to apply the necessary counterforce to the body lumen wall. In one example, a ratio of the length of the compression spring 220 to its spring constant may be from about 3:1 to about 300:1, and in one embodiment, from about 30:1 to about 125:1, or from about 35:1 to about 40:1.

Figure 24:
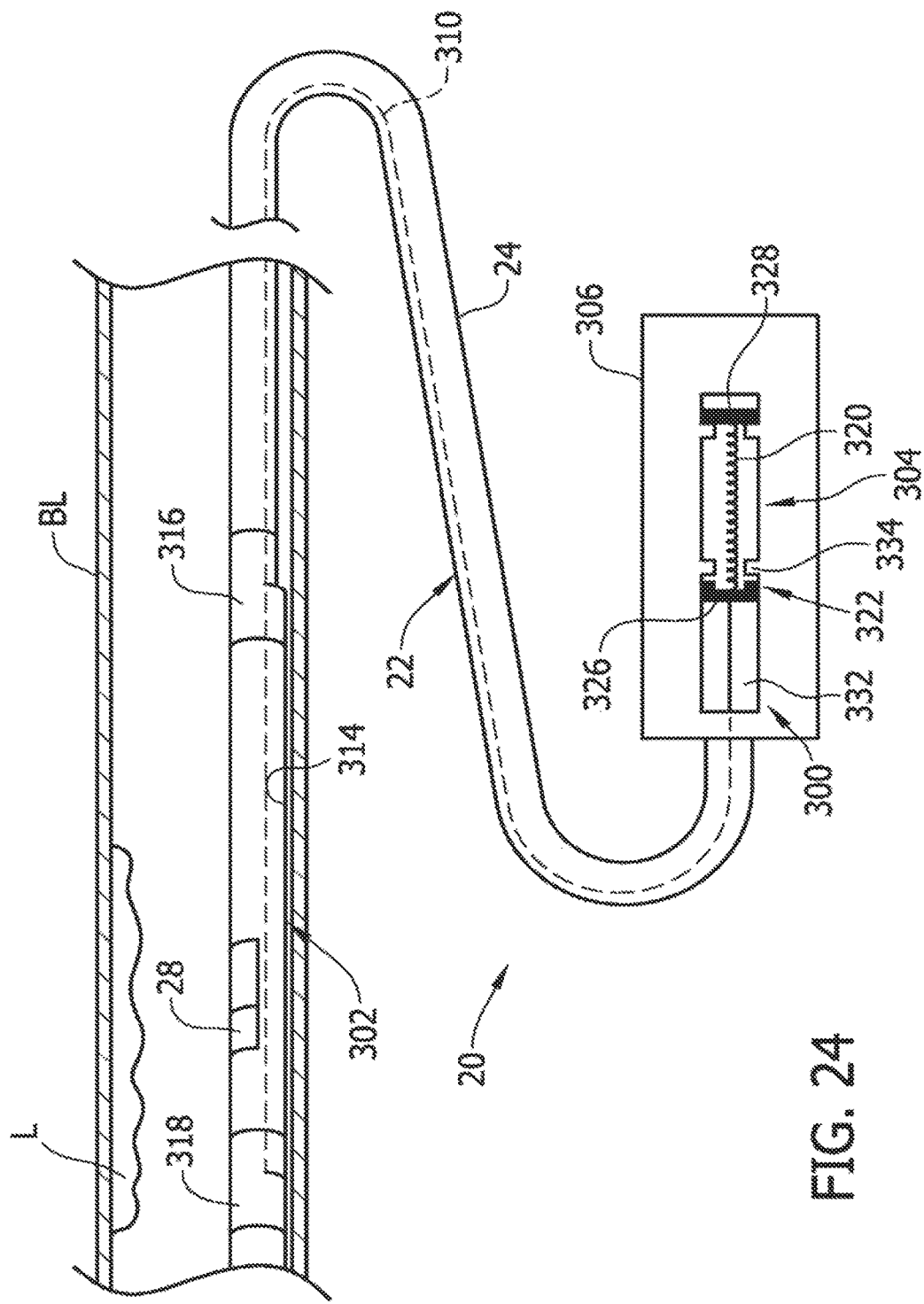
FIG. 24 is a schematic of a tissue-removing catheter including a third embodiment of the urging mechanism, the urging mechanism in a relaxed state.
Figure 25:
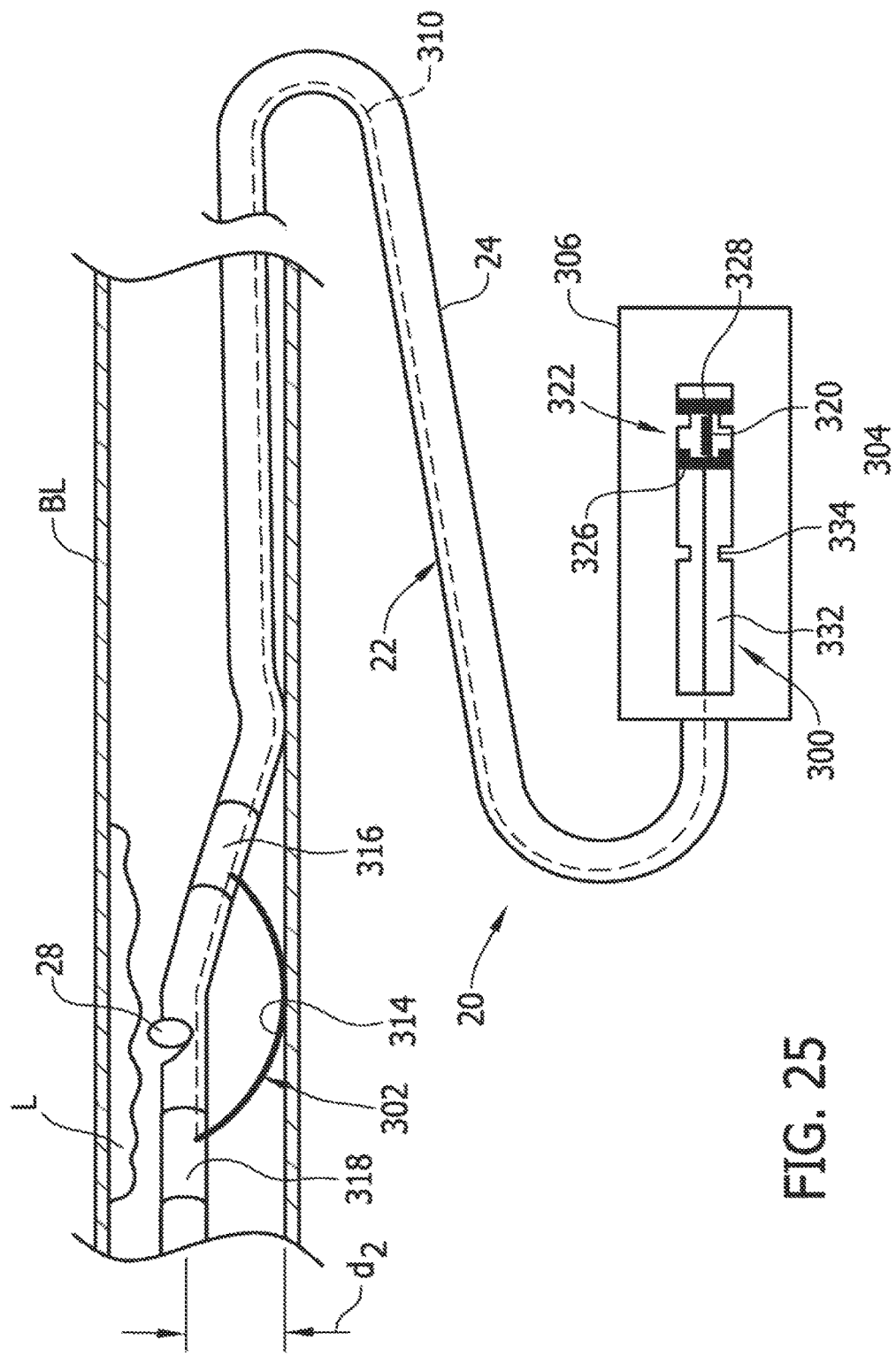
FIG. 25 is similar to FIG. 24, with the urging mechanism in an active state.

Referring to FIGS. 24 and 25, a third embodiment of an urging mechanism for selectively applying an urge force to the catheter body 22 to urge the cutter 28 against a wall of the body lumen BL (e.g., toward the lesion site) to enhance treatment is generally indicated at 300. This urging mechanism 300 can be used with the catheter illustrated in FIGS. 1-20, in lieu of the first embodiment of the urging mechanism, and as such, FIGS. 24 and 25 illustrate the urging mechanism as being part of the catheter illustrated in FIGS. 1-20, with like components indicated by corresponding reference numerals. It is understood that the urging mechanism 300 may be used with other types of tissue-removing catheters without departing from the scope of the present invention.

This urging mechanism embodiment 300 is similar to the second urging mechanism embodiment 200, with a main difference being the elastically compressible member 220 (e.g., the compression spring) of the second embodiment is replaced with an elastic tension member 320 (e.g., a tension spring). The urging mechanism 300 includes a deflection device, generally indicated at 302, adjacent the distal end of the proximal portion 24 of the catheter body 22, and a deflection-actuating device, generally indicated at 304, associated with a handle 306. An elongate tension-transmitting member (e.g., elongate pull member) 310 of the urging mechanism 300 operatively connects the deflection device 302 and the deflection-actuating device 304 for transmitting tensile force (e.g., pull force) to activate the deflection device 302. As explained in more detail below, when activated the deflection device 302 urges a portion of the catheter body 22 diametrically opposing the deflection device toward the wall of the body lumen (i.e., toward the lesion site). Moreover, in at least one embodiment, the deflection-actuating device 304 provides a counterbalance to the urge force applied to the body lumen wall by the deflection device 302 so that the deflection device applies a substantially constant urge force across a broad range of body lumen diameters.

In the illustrated embodiment, the deflection device 302 comprises a deflector 314 secured to the catheter body 22 via a fixed connector 318 and a longitudinally translatable connector 318 that is spaced apart from the fixed connector along the catheter body. In the illustrated embodiment, the longitudinally translatable connector 318 is distal of the cutter 28, and the fixed connector 316 is proximal of the cutter. A distal end portion of the deflector 314 is secured to the slidable connector 318, and a proximal end portion of the deflector is secured to the fixed connector 316. As such, the deflection device 302 is located adjacent to cutter 28 and generally diametrically opposes the cutter, relative to the catheter body 22, although the deflection device may be located elsewhere on the catheter body. One or both of the connectors 316, 318 may comprises a collar or sleeve that is fitted over the catheter body 22, or located inside the catheter body. The connectors 316, 318 may be of other types and configurations without departing from the scope of the present invention.

The deflector 314 is configurable between a non-deployed or stowed configuration (FIG. 24), in which the deflector does not impart an urge force to the catheter body 22, and a deployed configuration (FIG. 25), in which the deflector imparts an urge force to body lumen wall to urge the cutter 28 toward the lesion site L. As explained below, the tension-transmitting member 310 selectively imparts longitudinal movement (e.g., sliding) of the longitudinally translatable connector 318 relative to the catheter body 22 and the fixed connector 316 to deploy the deflector 314. In its non-deployed configuration, the deflector 314 has a low profile, and may be generally linear and generally parallel to the longitudinal axis of the catheter body 22. In its deployed configuration, the deflector 314 extends a transverse distance $d_2$ from the longitudinal axis of the catheter body 22 to apply an urge force against the body lumen wall and urge the cutter toward the lesion L. As explained in more detail below, the longitudinally translatable connector 318 allows the deflector 314 to be resiliently deflectable inwardly toward the longitudinal axis of the catheter body 22 to thereby decrease the transverse distance between the longitudinal axis of the catheter body and the deflector in response to a transverse force applied thereto by the body lumen wall. In the illustrated embodiment, the deflector 314 comprises one or more (e.g., two) generally flexible elongate members that buckle (e.g., bend) into a generally arcuate profile when the longitudinally translatable connector 318 is moved longitudinally relative to the catheter body 22 and the fixed connector 316. The deflector 314 may be formed, at least in part, from a shape memory material (e.g., nitinol), such that the deflector is resiliently biased in either the non-deployed, linear configuration or the deployed, arcuate configuration.

Referring to FIGS. 24 and 25, the deflection-actuating device 304 includes an elastic tension component 320 secured to the proximal end of the tension-transmitting member 310, and a load actuator 322 for selectively locking and unlocking the elastic tension component to selectively configure the deflector 314 between its respective non-deployed and deployed configurations. In one embodiment, the elastic tension component 320 comprises a tension spring that contracts proximally in length relative to the handle 306. In the illustrated embodiment a proximal portion of the tension-transmitting member 310 and a distal portion of the tension spring 320 are secured to a movable connector 326 of the load actuator 322 that is selectively movable relative to the handle 306, and a proximal portion of the tension spring 320 is secured to a fixed or anchored connector 328. The movable connector 326 is received in a track 332 and releasably lockable relative to the handle 306, such as by teeth 334 on the track. In an initial state when the deflector 314 is in its non-deployed configuration and the movable connector 326 is locked (FIG. 24), the tension spring 320 may be pre-loaded with an initial stored energy that is less than the maximum potential energy for the spring. For example, the tension spring 320 may be elongated from about 25% to about 75% of greater than its initial, unloaded length. Upon unlocking the movable connector 326, the tension spring 320 contracts toward the fixed connector 328, which imparts proximal movement of the movable deflector-connector 318, via proximal movement of the tension-transmitting member 310, to deploy the deflector 314.

The tension spring 320 applies a suitable force to the deflector 314 so that the deflector applies a suitable urge force to the body lumen BL when the deflector engages the body lumen wall. In one non-limiting example, where the deflector 314 is formed from nitinol or other shape-memory material or otherwise formed to be biased to its linear (i.e., non-deployed) configuration, the tension spring 320 applies a suitable counterforce to the deflector to both overcome the bias of the deflector and to apply a suitable force to the body lumen BL when the deflector engages the body lumen wall. In another non-limiting example, the deflector 314 may be biased in its deployed configuration. In other non-limiting examples, the deflector 314 may not be biased in either its non-deployed configuration or its deployed configuration.

In one embodiment, the tension spring 320 or other elastic tension component has a relatively small spring constant, which may be from about 0.02 lb/in to about 0.2 lb/in, or from about 0.04 lb/in to about 0.08 lb/in, or about 0.06 lb/in. Because the tension spring 320 has a relatively small spring constant, when the deflector 314 flattens out (i.e., takes on a more linear shape), such as when the catheter 20 enters a smaller diameter body lumen portion, the tension spring elongates a relatively small amount, which causes to a relatively small change in the force applied to the deflector because of the relatively small spring constant. Thus, the urge force applied by the deflector 314 to urge the cutter 28 toward the lesion remains substantially constant when the transverse distance $d_2$ between the longitudinal axis of the catheter body 22 and the deflector increases and decreases as the catheter moves through portions of the body lumen having different inner diameters. As used herein, to apply a "substantially constant urge force" means that when the catheter body moves from a 7 mm inner diameter body lumen portion to a 3 mm inner diameter body lumen portion, the transverse urge force applied to the body lumen wall increases less than 0.03 lb from the initial transverse urge force. In one example, the transverse urge force applied to the body lumen wall increases from about 0.01 lb to about 0.002 lb from the initial transverse urge force. Moreover, because of the configuration of the deflection device 202 (e.g., the deflector 214 being fixed to the body 222 at one end and axially slidable at the opposite end to impart force to the spring 220), the urge force applied by the deflector 314 against the body lumen wall is generally not directly proportional to the transverse distance $d_2$ between the longitudinal axis of the catheter body 22 and the deflector. Other ways of applying a substantially constant urge force against the body lumen wall as the catheter moves through portions of the body lumen having different inner diameters do not depart from the scope of the present invention.

Because of the relatively small spring constant, it takes relatively considerable displacement of the spring 320 to apply the necessary force to move the longitudinally movable connector 318 and deploy the deflector 314 and to apply the necessary urge force to the body lumen wall. In one example, a ratio of the length of the tension spring 320 to its spring constant may be from about 2.5:1 to about 225:1, and in one embodiment, from about 12.5:1 to about 75:1.

Figure 26:
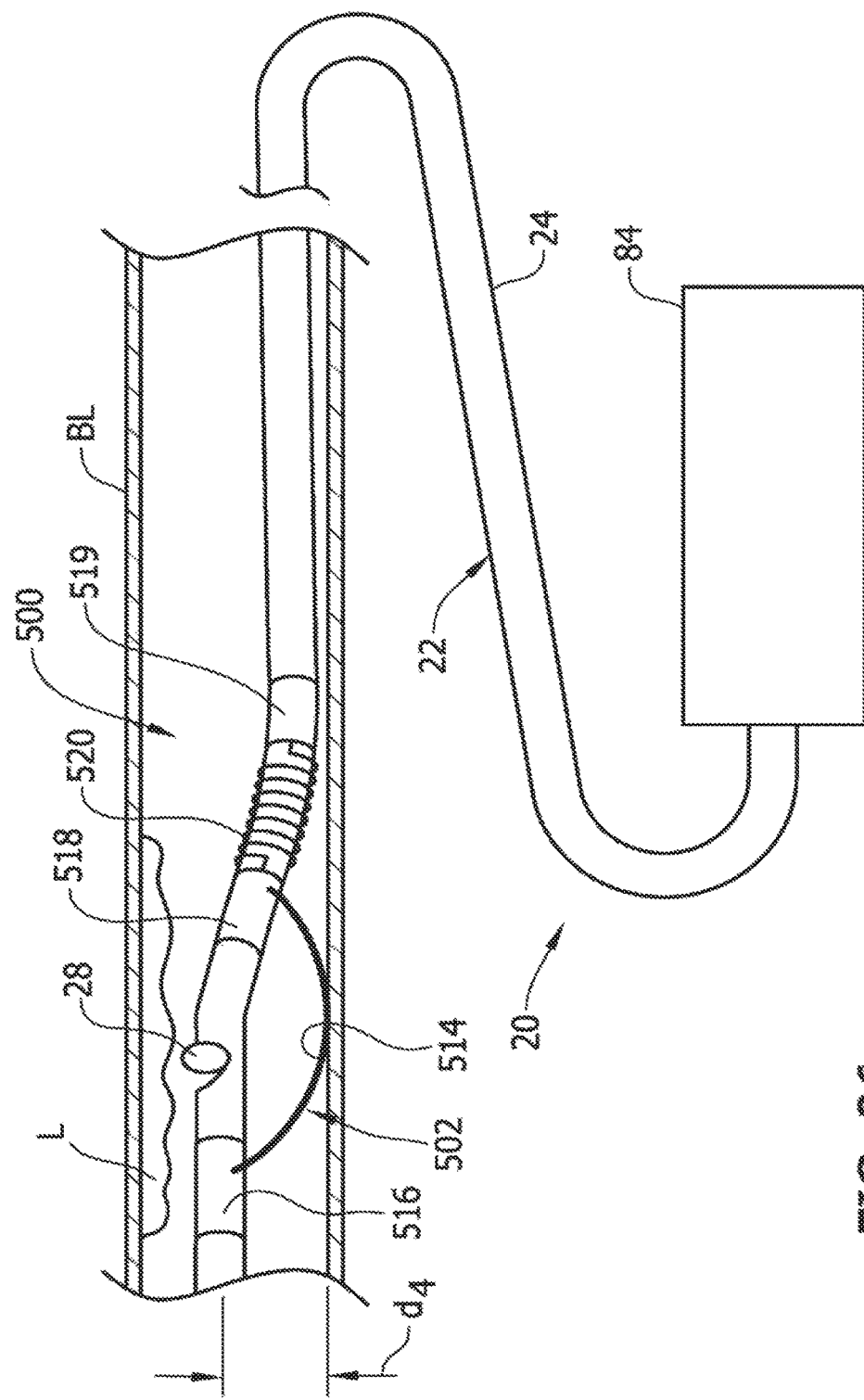
FIG. 26 is a schematic of a tissue-removing catheter including a fourth embodiment of the urging mechanism, the urging mechanism in an active state.

Referring to FIG. 26, a fourth embodiment of an urging mechanism for selectively applying an urge force to the body lumen wall to urge the cutter 28 toward the lesion site L to enhance treatment is generally indicated at 500. This urging mechanism 500 can be used with the catheter illustrated in FIGS. 1-20, in lieu of the first embodiment of the urging mechanism, and as such, FIG. 26 illustrates the urging mechanism as being part of the catheter illustrated in FIGS. 1-20, with like components indicated by corresponding reference numerals. It is understood that the urging mechanism 500 may be used with other types of tissue-removing catheters without departing from the scope of the present invention.

The present urging mechanism 500 is similar to the second embodiment of the urging mechanism 200, and like components are indicated by corresponding reference numerals plus 300. The main difference between the two embodiments is that the present embodiment does not include the compression-transmitting component 210, but instead, the present embodiment includes an elastic compression member (e.g., a compression spring) 520 connected between the longitudinally movable deflector-connector 518 and a second fixed deflector-connector 519 that is fixedly secured to the catheter body 22. The elastic compression member 520 is configured to resiliently urge the deflector 514 toward its deployed configuration. The deflector 514 is secured to the fixed deflector-connector 516, which is distal of the cutter 28, and the longitudinally movable deflector-connector 518, which is proximal of the cutter.

The compression spring 520 imparts a suitable force to the deflector 514 to apply a suitable urge force to the body lumen BL when the deflector 514 engages the body lumen wall. In one embodiment, the compression spring 220 or other elastically compressible component has a relatively small spring constant, which may be from about 0.02 lb/in to about 0.2 lb/in, or from about 0.04 lb/in to about 0.08 lb/in, or about 0.06 lb/in. Because the compression spring 520 has a relatively small spring constant, when the deflector 514 flattens out (i.e., takes on a more linear shape), such as when the catheter 20 enters a smaller diameter body lumen portion, the compression spring compresses a relatively small amount, which causes to a relatively small change in force applied to the deflector because of the relatively small spring constant. Thus, the transverse urge force applied by the deflector 414 to urge the cutter 28 toward the lesion L remains substantially constant when the transverse distance $d_4$ between the longitudinal axis of the catheter body 22 and the deflector increases and decreases as the catheter moves through portions of the body lumen having different inner diameters. As used herein, to apply a "substantially constant urge force" means that when the catheter body moves from a 7 mm inner diameter body lumen portion to a 3 mm inner diameter body lumen portion, the transverse urge force applied to the body lumen wall increases less than 0.03 lb from the initial transverse urge force. In one example, the transverse urge force applied to the body lumen wall increases from about 0.01 lb to about 0.002 lb from the initial transverse urge force. Moreover, because of the configuration of the deflection device 202 (e.g., the deflector 214 being fixed to the body 222 at one end and axially slidable at the opposite end to impart force to the spring 220), the urge force applied by the deflector 514 against the body lumen wall is generally not directly proportional to the transverse distance $d_4$ between the longitudinal axis of the catheter body 22 and the deflector. Other ways of applying a substantially constant urge force against the body lumen wall as the catheter moves through portions of the body lumen having different inner diameters do not depart from the scope of the present invention.

Because of the relatively small spring constant, it takes relatively considerable displacement of the spring 520 to apply the necessary force to move the longitudinally movable connector 518 and deploy the deflector 514 and to apply the necessary urge force to the body lumen wall. In one example, a ratio of the length of the compression spring 520 to its spring constant may be from about 3:1 to about 300:1, and in one embodiment, from about 30:1 to about 125:1, or from about 35:1 to about 40:1.

In one example, the deflector 514 is formed from nitinol or other shape-memory material or otherwise formed to be biased to its linear (i.e., flat) configuration. In this example, the compression spring 520 applies a suitable counterforce to the deflector to both overcome the bias of the deflector and to apply a suitable urge force to the body lumen BL when the deflector engages the body lumen wall. In another example, the deflector 514 is formed from nitinol or other shape-memory material or otherwise formed to be biased to its deployed configuration. The deflector 514 inherently produces an urge force to the catheter 20 when the deflector engages the body lumen wall to urge the cutter 28 toward the lesion because the deflector is resiliently biased to its deployed position. The elastic compression member 520, which may be preloaded, provides a restoring force to the deflector 514 so that as the catheter 20 moves into a larger diameter body lumen, the deflector, through its inherent resiliency and with assistance from the compression spring 520, rebounds to maintain engagement with the body lumen wall.

Figure 27:
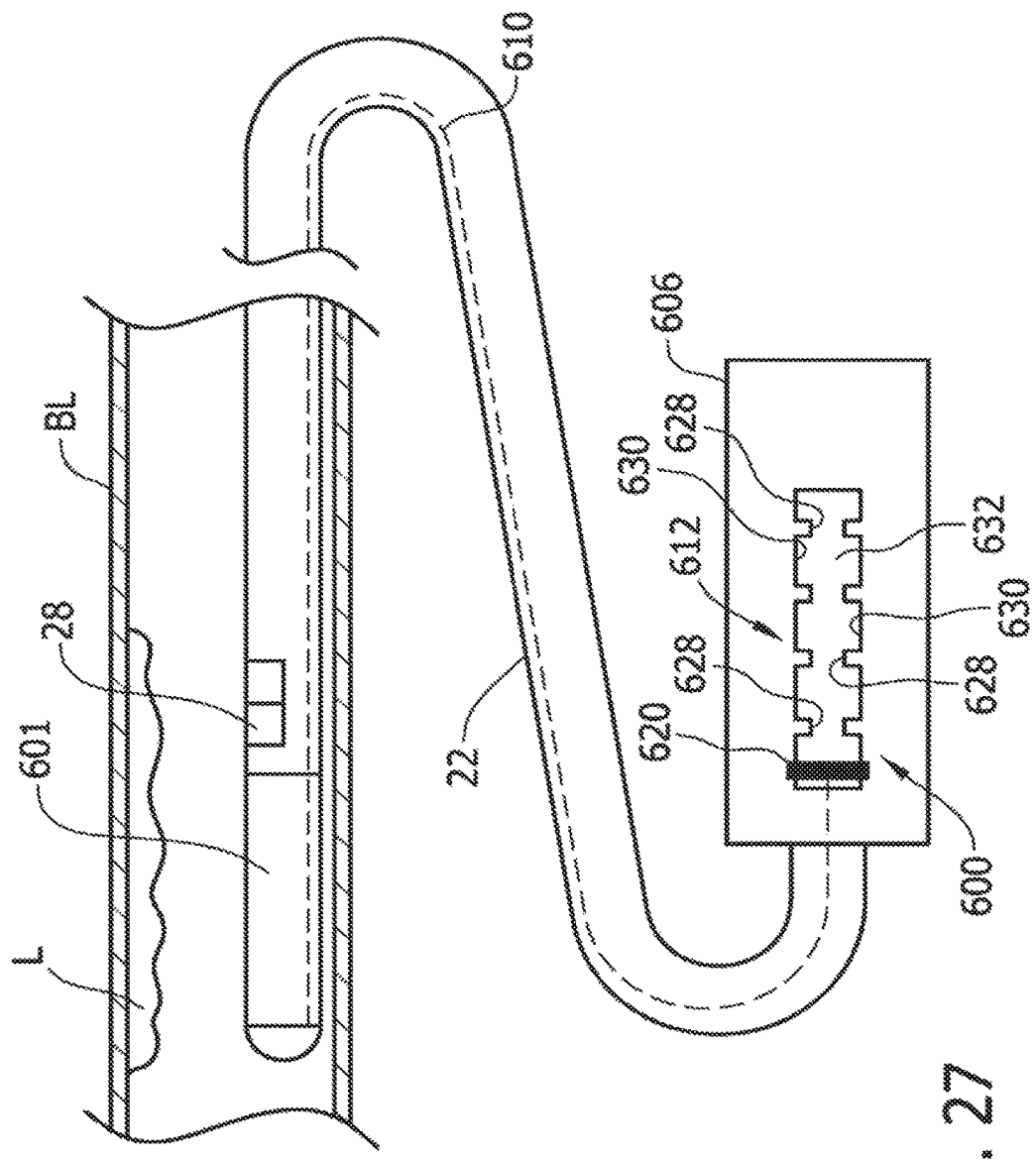
FIG. 27 is a schematic of a tissue-removing catheter including a fifth embodiment of the urging mechanism, the urging mechanism in a relaxed state.
Figure 28:
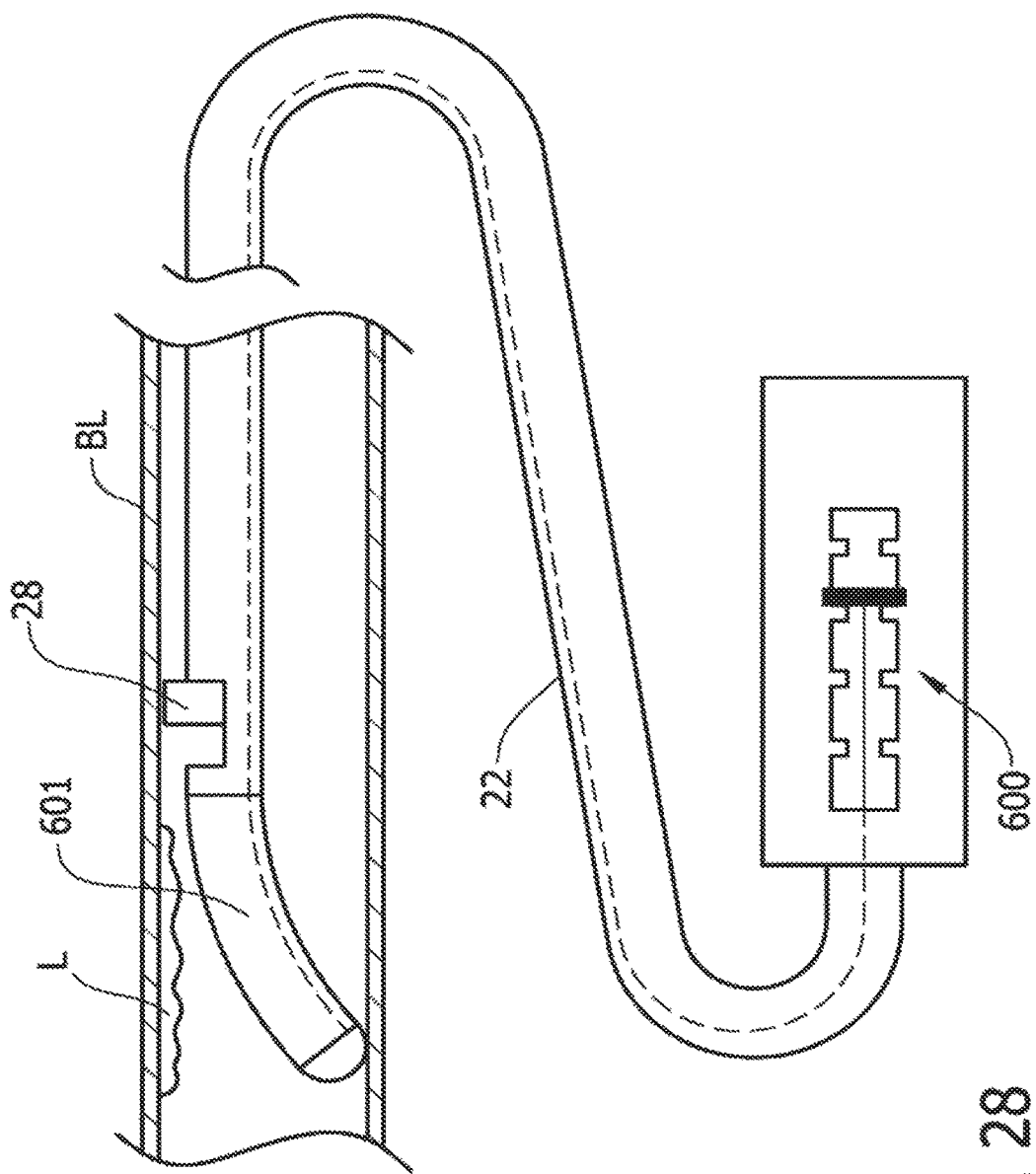
FIG. 28 is similar to FIG. 27, with the urging mechanism in an active state.

Referring to FIGS. 27 and 28, a fifth embodiment of an urging mechanism for selectively applying an urge force to urge the cutter 28 against a wall of the body lumen (e.g., toward the lesion site) to enhance treatment is generally indicated at 600. This urging mechanism 600 can be used with the catheter illustrated in FIGS. 1-20, in lieu of the first embodiment of the urging mechanism, and as such, FIGS. 27 and 28 illustrate the urging mechanism as being part of the catheter illustrated in FIGS. 1-20, with like components indicated by corresponding reference numerals. It is understood that the urging mechanism 600 may be used with other types of tissue-removing catheters without departing from the scope of the present invention.

The present urging mechanism 600 is similar to the first embodiment of the urging mechanism 100, and like components are indicated by corresponding reference numerals plus 500. The main difference between the two embodiments is that the present embodiment includes a flexible distal portion 601 that is selectively configurable between a non-urging configuration (FIG. 27) and an urging-configuration (FIG. 28) to urge the cutter 28 toward a lesion L. The urging mechanism 600 includes an elongate tension member 610 extending along the catheter body 22 (e.g., extending within a longitudinal lumen of the catheter body), which may be similar or identical to the tension member 110 of the first embodiment. A distal portion of the tension member 610 is fixedly secured to the flexible distal portion 601 (e.g., adjacent a distal end or tip of the distal portion). A proximal portion of the tension member 610 is secured to a tension-adjusting device, generally indicated at 612. In the illustrated embodiment, the tension-adjusting device 612 comprises a detent mechanism including a load actuator 620 received in a toothed track 632 for selectively applying a tensile load to the tension member 610. The tension-adjusting device 612 allows for selectively locking and unlocking the position of the load actuator 620 relative to the handle 606, which in turn, allows for selective, incremental adjustment (i.e., increasing and decreasing adjustment) of the tensile load applied to the flexible distal portion 601. The track 632 has teeth 628 spaced apart from one another along the length of the track to define a plurality of transverse slots 630, in which the load actuator 620 is selectively receivable and removable. The tension-adjusting device 612 may be of other types and configurations without departing from the scope of the present invention.

As shown in FIG. 27, when the load actuator 620 is in a distal position (i.e., a non-urging position) the flexible distal portion 601 is substantially linear and does not urge the cutter 28 toward the lesion L. Upon movement of the load actuator 620 proximally to an urging position (FIG. 28), the flexible distal portion 601 deflects relative to the catheter body 22 and the cutter 28. Deflection of the flexible distal portion 601 urges the distal portion against the body lumen wall and urges the cutter 28 toward the lesion L. As can be understood, the amount of deflection of the flexible distal portion 601 and/or the amount of urge force applied against the body lumen wall is adjustable via the tension-adjusting device 612. By allowing a user to adjust the amount of deflection of the flexible distal portion 601, the user can better control the cut depth as the cutter 28 passes through the lesion. Indicia or other indication markings (not shown) may be provided on the handle 606 to indicate the amount of deflection of the distal portion 601 being imparted at each incremental location of the actuator 120 along the track 126. Alternatively, or in addition, indicia or other indication markings on the handle 606 may inform the user of where the actuator 620 should be positioned in the track 632 based on the diameter of the body lumen BL.

In another example (not shown), the urging mechanism 600 may include an elastic tension member (e.g., a tension spring) that is elastically deformable (i.e., elastically elongatable) along its longitudinal axis when a tensile load is applied thereto. The elastic tension member may be secured between the tension member 610 and the load actuator 620 and be similar or identical to the elastic tension member, as disclosed above in the first embodiment. The elastic tension member provides a spring bias at the flexible distal portion toward a deflected configuration.

Having described the invention in detail, it will be apparent that modifications and variations are possible without departing from the scope of the invention defined in the appended claims.

When introducing elements of the present invention or the preferred embodiments(s) thereof, the articles "a", "an", "the" and "said" are intended to mean that there are one or more of the elements. The terms "comprising", "including" and "having" are intended to be inclusive and mean that there may be additional elements other than the listed elements. In view of the above, it will be seen that the several objects of the invention are achieved and other advantageous results attained.

As various changes could be made in the above constructions, products, and methods without departing from the scope of the invention, it is intended that all matter contained in the above description and shown in the accompanying drawings shall be interpreted as illustrative and not in a limiting sense.

What is claimed is:

1. A tissue-removing catheter for removing tissue from a wall of a body lumen during a cutting operation thereof, the tissue-removing catheter comprising:
    an elongate catheter body configured for insertion into the body lumen, the catheter body having opposite distal and proximal portions, and a longitudinal axis extending between the distal and proximal portions, the catheter body having a jogged portion configured to apply an urge force against the body lumen wall and urge a portion of the catheter body toward a portion of the body lumen wall;
    a tissue-removing element for removing tissue from the body lumen during the cutting operation, the tissue-removing element being located generally adjacent the portion of the catheter body that is urged toward the body lumen wall by the jogged portion;
    an urging mechanism configured to selectively apply a compressive load to the catheter body to adjust the bending stiffness of the jogged portion and the urge force applied by the jogged portion,
    wherein the catheter body is configured to retain the shape of the jogged portion when the urging mechanism is applying a compressive load to the catheter body.

2. The tissue-removing catheter set forth in claim 1, wherein the urging mechanism includes a tension member for imparting the compressive load to the catheter body.

3. The tissue-removing catheter set forth in claim 2, wherein the tension member is elongate and extends along the catheter body.

4. The tissue-removing catheter set forth in claim 3, wherein the tension member is generally non-elongatable.

5. The tissue-removing catheter set forth in claim 3, wherein the tension member is movable longitudinally with respect to the catheter body.

6. The tissue-removing catheter set forth in claim 5, wherein the tension member has a distal portion adjacent the distal portion of the catheter body, and an opposite proximal portion adjacent the proximal portion of the catheter body, the distal portion of the tension member being fixedly secured to the catheter body.

7. The tissue-removing catheter set forth in claim 6, wherein the distal portion of the tension member is fixedly secured to the catheter body at a location distal of the jogged portion.

8. The tissue-removing catheter set forth in claim 7, further comprising a fixed connector secured to the catheter body at a location distal of the jogged portion, wherein the distal portion of the tension member is fixedly secured to the fixed connector.

9. The tissue-removing catheter set forth in claim 7, wherein the tension member comprises a flexible wire.

10. The tissue-removing catheter set forth in claim 6, wherein the urging mechanism includes an elastic tension component for imparting a tensile load to the tension member, and a load actuator for imparting a tensile load to elastic tension component.

11. The tissue-removing catheter set forth in claim 10, wherein the elastic tension component is secured to the proximal portion of the tension member.

12. The tissue-removing catheter set forth in claim 11, wherein the elastic tension component is elastically elongatable along a length of the elastic tension component.

13. The tissue-removing catheter set forth in claim 12, wherein the elastic tension component has a longitudinal axis that is generally parallel or generally coaxial to the longitudinal axis of the catheter body at the proximal portion of the catheter body.

14. The tissue-removing catheter set forth in claim 12, wherein the load actuator is fixedly secured to the elastic tension component adjacent a proximal end of the elastic tension component.

15. The tissue-removing catheter set forth in claim 14, wherein the load actuator is configured for selectively elongating the elastic tension component.

16. The tissue-removing catheter set forth in claim 15, wherein the load actuator is selectively lockable in a plurality of positions to allow for selective, incremental adjacent of the tensile load applied to the tension member via the elastic tension component.

17. The tissue-removing catheter set forth in claim 1, wherein the urging mechanism is configured to selectively apply a plurality of incremental compressive loads to the catheter body, each of which adjusts the bending stiffness of the jogged portion and the urge force applied by the jogged portion.

18. The tissue-removing catheter set forth in claim 1, wherein urging mechanism is configured to selectively apply zero compressive load to the catheter body such that the urging mechanism has no effect on the bending stiffness of the jogged portion and no effect on the urge force applied by the jogged portion.

19. The tissue-removing catheter set forth in claim 1, wherein the urging mechanism continuously applies the compressive load to the catheter body.

* * * * *